US008067364B2

(12) United States Patent
Coates et al.

(10) Patent No.: US 8,067,364 B2
(45) Date of Patent: Nov. 29, 2011

(54) DEER ANTLER EXTRACT FOR PROMOTING ANGIOGENESIS

(75) Inventors: Dawn Elizabeth Coates, Mosgiel (NZ); Stephen Roy Haines, Mosgiel (NZ); James Miller Suttie, Mosgiel (NZ)

(73) Assignee: Velvet Antler Research New Zealand Limited (VARNZ), Mosgiel (NZ)

( * ) Notice: Subject to any disclaimer, the term of this patent is extended or adjusted under 35 U.S.C. 154(b) by 205 days.

(21) Appl. No.: 12/470,372

(22) Filed: May 21, 2009

(65) Prior Publication Data

US 2009/0238892 A1 Sep. 24, 2009

Related U.S. Application Data

(62) Division of application No. 10/555,043, filed as application No. PCT/NZ2004/000101 on May 26, 2004, now abandoned.

(30) Foreign Application Priority Data

May 27, 2003 (NZ) ...................................... 526157

(51) Int. Cl.
*A61K 38/17* (2006.01)
*A61K 38/18* (2006.01)
*C07K 14/475* (2006.01)
*C07K 1/00* (2006.01)
(52) U.S. Cl. .......... 514/7.6; 514/9.4; 530/350; 530/399; 530/412
(58) Field of Classification Search .................. None
See application file for complete search history.

(56) References Cited

U.S. PATENT DOCUMENTS

| 5,147,782 | A | 9/1992 | Brocks et al. |
| 5,705,477 | A | 1/1998 | Sporn et al. |
| 2003/0203001 | A1 | 10/2003 | Schultz |

FOREIGN PATENT DOCUMENTS

| RU | 2112524 C1 | 6/1998 |
| SU | 1822785 A1 | 6/1993 |
| WO | WO 2004/083154 A1 | 9/2004 |

OTHER PUBLICATIONS

Zhou, Q-L, et al. 1999 Acta Pharmacologica Sinica 20(3): 279-282.*
Singer et al. 1999 NEJM 341(10): 738-746.*
BD bioscience endothelial cells reference sheets, 2010, 7 pages.*
Drugs.com chronic wounds reference sheets, 2008, 3 pages.*
Ekstrand A.J. et al. 2003 "Deletion of neuropeptide Y (NPY) 2 receptor in mice results in blockage of NPY-induced angiogenesis and delayed wound healing" *Proc Natl Acad Sci USA* 100:6033-6038.
Ketterer, B. et al. 1976 "A low-molecular-weight protein from rat liver that resembles ligand in its binding properties" *Biochem J* 155:511-521.
Ko et al., "Epidermal Growth Factor From Deer (*Cervus elaphus*) Submaxillary Glad and Velvet Antler" General and Comparative Endocrinology 63, pp. 431-440, 1986.
Latest Research http:www.deervelvetinformation.org/research.htm, Apr. 4, 2003 http:www.archive.org/, used to establish the publication date of the document see whole document, pp. 1-12 downloaded on Aug. 26, 2004.
Latest Research http:www.velvita.com/latestresearch.htm, Apr. 7, 2003 http:www.archive.org/, used to establish the publication date of the document see whole document, pp. 1-13 downloaded on Aug. 26, 2004.
Lu, L. et al. 2000 "An experimental study on wound healing with exogenous hyaluronic acid" *Zhonghua Zheng Xing Wai Ke Za Zhi* 16:30-33, Abstract Only.
Muzzarelli, R.A. et al. 1999 "Biochemistry, histology and clinical uses of chitins and chitosans in wound healing" *EXS* 87:251-264, Abstract Only.
Montesano, R. et al. 1996 "Synergistic effect of hyaluronan oligosaccharides and vascular endothelial growth factor on angiogenesis in vitro" *Lab Invest* 75:249-262, Abstract Only.
NCB/NLM/NIH Reference Sheet for "Endothelial Cells" (2 pages); downloaded on Nov. 17, 2008.
NCB/NLM/NIH Reference Sheet for "Endothelium" (2 pages); downloaded on Nov. 17, 2008.
Roberts, A.B. et al. 1980 "Transforming growth factors: isolation of polypeptides from virally and chemically transformed cells by acid/ethanol extraction" *Proc Natl Acad Sci USA* 77:3494-3498.
Scopes, Robert K. in *Protein Purification—Principles and Practice*, Third Edition Springer Verlag, 1994, see Sections 4.4 and 4.7.
Slevin, M. et al. 1998 "Angiogenic oligosaccharides of hyaluronan induce protein tyrosine kinase activity in endothelial cells and activate a cytoplasmic signal transduction pathway resulting in proliferation" *Lab Invest* 78:987-1003, Abstract Only.
Slevin, M. et al. 2002 "Angiogenic oligosaccharides of hyaluronan induce multiple signaling pathways affecting vascular endothelial cell mitogenic and wound healing responses" *J Biol Chem* 277:41046-41059, Abstract Only.
Sunwoo, H.H. et al. 1998 "Isolation, characterization and localization of glycosaminoglycans in growing antlers of wapiti (*Cervus elaphus*)" *Comp Biochem Physiol B Biochem Mol Biol* 120:273-283, Abstract Only. Weng et al., "A New Polypeptide Promoting Epidermal Cells and Chondrocytes Proliferation From *Cervus elaphus* Linnaeus" Acta Pharmaceutica Sinica , 36(12), pp. 913-916, 2001.
Weng et al. 2001 "Velvet antler polypeptides promoted proliferation of epidermal cells and fibroblasts and skin wound healing" *Acta Pharmaceutical Sinica* 36(11):817-820. (English Translation).
Baranoski, S. and Ayello, E.A. 2008 in *Wound Care Essentials Practice Principles*, Second Edition, Wolters Kluwer Health, Lippincott Williams & Wilkins; Ambler PA, p. 75.
Bennett, N.T. and Schultz, G.S. 1993 "Growth factors and wound healing: Part II. Role in normal and chronic wound healing" *The American Journal of Surgery* 166:74-81.
Bucalo, B. et al. 1993 "Inhibition of Cell proliferation by chronic wound fluid" *Wound Repair Regen* 1(3): 181-186.

(Continued)

*Primary Examiner* — Marsha Tsay
(74) *Attorney, Agent, or Firm* — Knobbe Martens Olson & Bear LLP

(57) ABSTRACT

An isolated extract of deer velvet which contains components which have molecular weights that are substantially are less than or equal to 10 kDa and which have a proliferative effect on endothelial cells and/or promote angiogenesis.

6 Claims, 15 Drawing Sheets

OTHER PUBLICATIONS

Cook, H. et al. 2000 "Defective extracellular matrix reorganization by chronic wound fibroblasts is associated with alterations in TIMP-1, TIMP-2, and MMP-2 activity" *J Investigative Dermatology* 115:225-233.

Cunningham, A.B. et al. 2001 in *The Biofilms Hypertextbook*, available online at (http://biofilmbook.hypertextbookshop.com/public_version/contents/chapters/chapter003/section003/blue/page001.html).

Lobmann, R. et al. 2002 "Expression of matrix-metalloproteinases and their inhibitors in the wounds of diabetic and non-diabetic patients" *Diabetologia* 45:1011-1016.

Seah, C.C. et al. 2005 "Chronic wound-fluid suppresses proliferation of dermal fibroblasts through a ras-mediated signaling pathway" *J Investigative Dermatology* 124:466-474.

Shukla, A. et al. 1998 "Differential expression of proteins during healing of cutaneous wounds in experimental normal and chronic models" *Biochemical and Biophysical Research Communications* 244:434-439.

Stojadinovic, O. et al. 2005 "Molecular pathogenesis of chronic wounds" *American Journal of Pathology* 167:59-69.

* cited by examiner

DEER ANTLER EXTRACT FOR PROMOTING ANGIOGENESIS

RELATED APPLICATIONS

This application is a divisional of application Ser. No. 10/555,043, filed Aug. 28, 2006, which is United States National Phase under 35 U.S.C. §371 of International Application PCT/NZ2004/000101, filed May 26, 2004 designating the U.S., and published in English as WO 2004/106372 on Dec. 9, 2004, which claims priority to New Zealand Patent Application No. NZ 526157, filed May 27, 2003.

BACKGROUND OF THE INVENTION

1. Field of the Invention

This invention relates to a deer antler extract. In particular, the present invention relates to angiogenic extracts obtained from deer antler velvet, and compositions containing said extracts for use in the treatment of wounds, injuries and diseases in human and animal medical practice.

2. Description of the Related Art

Wounds, in particular persistent wounds, which are difficult to heal, require a blood supply that can nourish the wound and mediate the healing process and minimize scar formation. Generally, most commonly used therapies for treating persistent wounds do not assist the wound to provide its own blood supply and therefore the healing process is slow.

Various therapies for the treatment of chronic wounds exist, however, the use of compression bandages still appears to be a common treatment (Marshall et al., 2001). Other therapies are available and some natural therapies have been proposed that work through mechanisms involving regulation of oxygen tension, and thus support hyperbaric oxygen treatments (Sen et al., 2002).

The healing of wounds by increasing angiogenesis (the process of vascularisation of tissues) is apparent with some proposed therapies. In a recent study adenosine appears to have increased the rate at which wounds healed by acting as an adenosine A(2A) receptor agonist (Montesinos et al., 2002). This resulted in increased numbers of micro vessels in the treated wounds. Increased angiogenesis is a likely mechanism underlining the improved healing shown in this paper.

The well known classical angiogenic growth factor Vascular Endothelial Growth Factor (VEGF) has been shown to cause angiogenesis and enhanced wound healing, when delivered by gene therapy to ensure local sustained delivery (Deodato et al., 2002). Malinda et al. (1998) have found that Thymosin α1 stimulates endothelial cell migration, angiogenesis, and wound healing, also confirming it as a potential wound healing agent.

Deer antlers are cast and regenerate annually. The antler grows at up to 2 cm a day during its growth phase, during which time it is termed 'velvet antler'. The growth is driven by a population of stem cells found in mesenchymal tissue at the tip of the antler (Li et al., 2002). Velvet antler is highly vascularised and blood vessels within the antler must grow at the same rate as the antler to support antler growth. We have identified this system as a potential source of angiogenic factors that will support wound healing processes.

There is one paper that suggests that the healing or regenerating pedicle, which they called the blastema, may have angiogenic potential (Auerbach et al., 1976). This paper involved the author screening a variety of tissues including antler blastema with the aim of showing that some tissues contained angiogenic potential. Importantly however, this paper did not contain any data showing actual angiogenic or wound healing activity. Blastema referred to the healing tissue which appears once the antler has cast, and is different from the more mature growing antler which the inventors have studied and outline in this specification.

There are no published reports of growing deer velvet antler being investigated in relation to its angiogenic effects. The inventors have found that total protein extracts of growing velvet do contain angiogenic factors.

The research outlined in this specification shows that extracts of deer velvet which contain these angiogenic factors are extracted from throughout the antler and are not just concentrated within the growing antler tip.

The inventors have prepared a composition of isolated peptides extracted from deer velvet antler which has an angiogenic effect and can be used to heal wounds.

The inventors fractionated velvet to assess the angiogenic potential. As part of the fractionation process they investigated high and low molecular weight fractions of velvet, and were surprised to find that the low molecular weight fraction had good activity. This was an encouraging result as smaller molecules are more likely to be stable and not degrade so rapidly within a wound.

Based on their molecular weights, most classical angiogenic growth factors would be expected to be found in the high molecular weight fraction, one exception to this rule would be the Thymosin family of peptides.

All references, including any patents or patent applications cited in this specification are hereby incorporated by reference. No admission is made that any reference constitutes prior art. The discussion of the references states what their authors assert, and the applicants reserve the right to challenge the accuracy and pertinence of the cited documents. It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

It is an object of the present invention to address the foregoing problems or at least to provide the public with a useful choice.

Further aspects and advantages of the present invention will become apparent from the ensuing description which is given by way of example only.

SUMMARY OF THE INVENTION

According to one aspect of the present invention there is provided an isolated extract of deer velvet which contains components which have molecular weights that are substantially less than or equal to 10 kDa and which have a proliferative effect on endothelial cells and/or promote angiogenesis.

According to another aspect of the present invention there is provided an isolated extract of peptides obtained from deer velvet wherein the peptides have molecular weights that are substantially less than or equal to 10 kDa and which have a proliferative effect on endothelial cells and/or promote angiogenesis.

According to another aspect of the present invention there is provided an isolated extract substantially as described above wherein the components retain the angiogenic effect on endothelial cells and/or promote angiogenesis even after processing which may subject the components to at least one of the following processes: heating to substantially 100° C. for up to substantially 3 min; sterilisation by exposure to over 2.5 Mrads of γ-irradiation; or freeze thawing.

According to another aspect of the present invention there is provided an isolated extract substantially as described above wherein the peptides retain the proliferative effect on endothelial cells, and/or promote angiogenesis even after processing which may subject the peptides to at least one of the following processes: heating to substantially 100° C. for up to substantially 3 min; sterilisation by exposure to over 2.5 Mrads of γ-irradiation; or, freeze thawing.

According to another aspect of the present invention there is provided the use of components extracted from deer velvet in the manufacture of a medicament for the treatment of wounds.

According to another aspect of the present invention there is provided the use of peptides extracted from deer velvet in the manufacture of a medicament for the treatment of wounds.

According to another aspect of the present invention there is provided the use of components extracted from deer velvet in the manufacture of a medicament for the treatment of persistent wounds.

According to another aspect of the present invention there is provided the use of peptides extracted from deer velvet in the manufacture of a medicament for the treatment of persistent wounds.

According to a further aspect of the present invention there is provided an isolated extract which contains at least one component from the extract substantially as described above wherein the component has a proliferative effect on endothelial cells and/or promotes angiogenesis.

According to a further aspect of the present invention there is provided an isolated extract which contains at least one peptide from the extract substantially as described above wherein the peptide has a proliferative effect on endothelial cells and/or promotes angiogenesis.

According to a further aspect of the present invention there is provided a composition which includes a therapeutically effective amount of the component substantially described above for the treatment of wounds.

According to a further aspect of the present invention there is provided a method of treating a wound comprising administering a composition substantially described above to an animal in need thereof.

According to a further aspect of the present invention there is provided a composition which includes a therapeutically effective amount of the peptide substantially described above for the treatment of wounds.

BRIEF DESCRIPTION OF THE DRAWINGS

Further aspects of the present invention will become apparent from the following description which is given by way of example only and with reference to the accompanying drawings in which.

DETAILED DESCRIPTION OF THE PREFERRED EMBODIMENT

Figure 1:
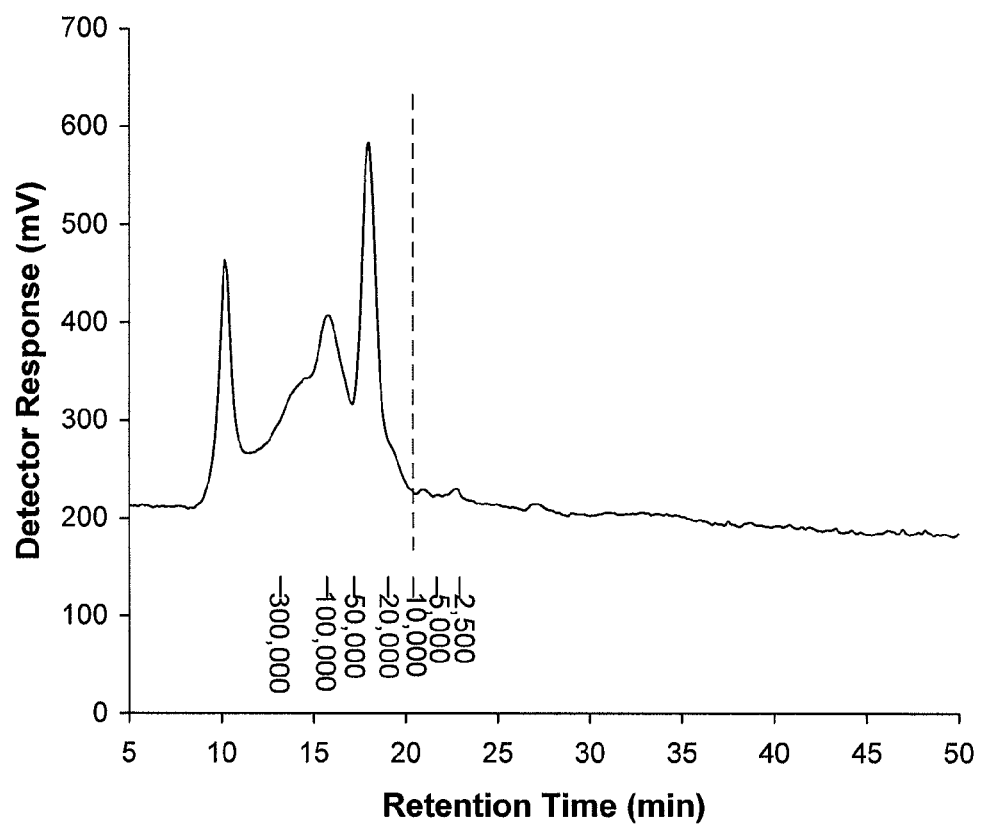
FIG. 1. Gel Filtration Chromatography Profile of high molecular weight fraction of deer velvet as derived by ultrafiltration of total protein extract. An approximate molecular weight scale is shown below the chromatogram and the Broken Line marks the expected elution position of 10 kDa proteins.

It is envisaged that the composition may take a variety of different formulations without departing from the scope of the present invention. For example, the composition may be formulated as: a gel, a lotion, a balm, a spray, a transdermal dressing, or such like, as would be apparent to a person skilled in the art.

The term 'peptide(s)' as used herein refers to any peptide or combination of peptides present in deer velvet including peptides, proteins and polypeptides which include polymers of amino acids; and also includes peptides, proteins and polypeptides which have been modified to include other moieties including but not limited to carbohydrate and/or lipid moieties.

The term 'component(s)' as used herein refers to any component or combination of components present in deer velvet including but not limited to peptides, carbohydrates, nucleic acids, free amino acids, lipids and growth factors.

The term 'proliferative effect' as used herein relates to the ability of the extracts or compositions of the present invention to cause cells and/or tissue to grow rapidly and/or multiply to produce new cells or tissue.

The term 'endothelial cells' as used herein relates to cells that make up the endothelium which lines the internal surface of blood vessels. This includes both venous and arterial blood vessels, as well as capillaries, the coronary vessels and the internal lining of the heart.

The term 'wound' as used herein refers to an injury in which skin, tissue or an organ is torn, pierced, cut, or otherwise divided or breached, as a result of disease, accident or surgery. This term refers to sores or lesions; including ulcers.

The term 'persistent wound(s)' as used herein refers to wounds which are slow to heal and last for a long time. This term may also refer to chronic wounds.

The term 'freeze thawing' as used herein refers to subjecting the peptides of the present invention to substantially −20° C. then rising to room temperature being substantially 18-25° C.

The molecular weights of the peptides of the present invention may be determined by a variety of different methods without departing from the scope of the present invention.

Generally, the molecular weights of the peptides of the present invention may be determined by Gel Filtration Chromatography, electrophoresis, mass spectrometry or other suitable method.

The terms 'Deer Velvet', 'Velvet', or 'Antler' as used herein refer to any part of the growing antler. In general, all tynes and the complete main beam of the antler may be included. However, in preferred embodiments the velvet skin may be removed when making angiogenic extracts and the base region of the main beam adjacent to and below the brow tyne may also be excluded.

Deer velvet is a complex tissue that, once dried, is comprised mainly of peptides, proteins and minerals but also contains other components such as carbohydrates, lipids and free amino acids. Extracts of deer velvet may therefore contain a mixture of all such components that are soluble in the extraction solvent. When aqueous extraction conditions are used the major components of the extract are reasonably expected to be peptides or proteins (Sunwoo et al., 1995).

Generally the deer velvet will be taken from red deer. However, other species of deer, such as wapiti, fallow or white tail, may also be used as a source of deer velvet.

The term 'Angiogenic' or 'Angiogenesis' as used herein refer to the ability of a substance to induce the growth of blood vessels.

Preferably, velvet is collected during the growing phase. However, this should not be seen as limiting the scope of the present invention as velvet from mature antler could also be collected and used for the present invention.

The velvet may be processed to preserve the velvet by one or more of the following methods; freeze-drying, freezing, hot dipping or oven drying. However this should not be seen as limiting the scope of the present invention.

Preferably, the velvet may be processed by hot dipping.

The components of the present invention may include any pharmaceutically or veterinarily acceptable carrier, excipient, stabilizer and/or other formulation additive: as would be apparent to a person skilled in the art.

The deer velvet may be extracted by a variety of different methods without departing from the scope of the present invention.

In one preferred embodiment the extraction may utilise organic solvents.

In another preferred embodiment the extraction may utilise aqueous solutions.

The term "total protein extract" as used herein refers to an aqueous extract prepared without any attempt to control the molecular weights of the peptides or proteins contained in the extract. By definition total protein extracts will also contain other water-soluble components of deer velvet that are not peptides or proteins, but are co-extracted with the peptides or proteins.

The deer velvet extract of the present invention may be fractionated to yield a low molecular weight fraction by a variety of different methods, such as ultrafiltration, gel filtration chromatography, dialysis, or by using organic solvents. However, this list should not be seen as limiting the scope of the present invention as other suitable methods may also be employed.

In one preferred embodiment the fractionation method may utilize 70% ethanol as the organic solvent in which deer velvet is soaked prior to aqueous extraction. The term "extract following ethanol pre-treatment" is used herein to refer to an extract prepared using this method.

In another preferred embodiment the fractionation method may utilise addition of cold ethanol to an aqueous solution of a deer velvet total protein extract, to cause the precipitation of high molecular weight proteins which are then removed by centrifugation or filtration. The term "ethanol precipitated extract" is used herein to refer to an extract prepared using this method.

In a further embodiment the fractionation method may utilise ultrafiltration.

Generally, the final velvet extract of the present invention may be an aqueous solution, a dried amorphous solid or a freeze-dried powder. However this should not be seen as limiting the scope of the present invention.

Preferably the aqueous solution may be in water, phosphate buffered saline (PBS) or other suitable aqueous solvent.

In addition to the disclosure contained herein regarding the preferred method of extraction, further details relating to extraction which may be of assistance to a person skilled in the art may be found in NZ 524868 and PCT application No. NZ2004/000058.

Thus, preferred embodiments of the present invention may have a number of advantages over the prior art which can include:

1. Providing an extraction method for obtaining angiogenic compositions from deer velvet.
2. Providing a composition from deer velvet which has angiogenic effects.
3. Providing a composition from deer velvet which can be used in the treatment of wounds or injuries.
4. Providing a composition from deer velvet which can be used in the treatment of persistent wounds.

Experimental
Methods
Collection of Tissue:

Deer velvet antlers were collected from 3-year-old red deer stags at 55-60 days of growth following casting of the previous antlers.

The velvet was removed according to the regulations laid down by Code of Recommendations and Minimum Standards for the Welfare of Deer during the Removal of Antlers, July 1992 (revised 1997), Ministry of Agriculture and Fisheries, Wellington, New Zealand.

The velvet was commercially processed by hot dipping or freeze-drying. Hot dipping is based on the traditional Chinese method, where sticks of antler are suspended from the base (i.e. tips downwards) and repeatedly dipped into almost boiling water for brief periods of time. After being dipped, they are allowed to cool before being dipped again. Dipping continues until clear plasma bubbles from the cut bases of the antlers. Antlers are then placed in a low humidity drier at approximately 15° C. for several weeks until they are dry.

Processed antlers (Hot Dipped or Freeze-Dried) were selected. The skin of the velvet was removed from the antler using a sharp knife. All parts of the red deer antlers at 55-60 days of growth were included except the base regions of the main sticks which were excluded up to and including the brow tynes. The velvet was sliced with a bandsaw in 1-2 cm thick rings and then chopped with a chisel into small blocks several centimeters in size before being ground into a powder using a mill (Thomas, USA) fitted with a 0.5 mm screen.

Extraction and Fractionation

The deer velvet is extracted and is fractionated to yield a low molecular weight fraction which is rich in angiogenic growth factors. This fraction can be made in multiple ways including ultrafiltration, dialysis, gel filtration chromatography, precipitation of high molecular weight proteins from solution by use of organic solvents (e.g. ethanol) or by aqueous extraction following pre-treatment of deer velvet with organic solvents e.g. 70% ethanol. The three methods used here for production of the extract have been by ultrafiltration, via precipitation of high molecular weight using ethanol, and via aqueous extraction following pre-treatment of deer velvet with 70% ethanol.

Extraction of Deer Velvet and Fractionation by Ultrafiltration
Preparation of a Total Protein Extract of Deer Velvet A Phosphate Buffer extract was made from 5 g of freeze dried velvet powder using 100 ml of phosphate buffer. The phosphate buffer contained di-sodium hydrogen orthophosphate (1.15 g/L), potassium di-hydrogen orthophosphate (0.24 g/L), potassium chloride (0.2 g/L) and sodium chloride (8.0 g/L). The mixture was stirred for an hour at room temperature and was then filtered through glass fibre filter paper (Whatman GF/A). The filtrate was centrifuged at 11,500 rpm for 30 minutes at 4° C. The supernatant (93 ml) was decanted into weighed Schott bottles and was shell frozen before being freeze-dried at 15° C.

Fractionation of the Total Protein Extract of Deer Velvet by Ultrafiltration

The Phosphate Buffer velvet extract (15 mg) was dissolved in deionised water at a concentration of 1 mg/ml and was decanted into an ultrafiltration device (Centriprep-YM10, Amicon, USA) having a nominal molecular weight cut off of 10 kDa. The tube was centrifuged at 2,100 g for 40 minutes at 4° C. The ultrafiltrate was removed after this time and the tube similarly centrifuged a further two times for 20 minutes each until only a small amount of high molecular weight retentate remained. The ultrafiltrates were combined and decanted into a fresh Centriprep tube. The ultrafiltration was repeated to ensure there was no contamination with high molecular weight proteins. The final ultrafiltrate containing the low molecular fraction was freeze-dried, weighed, and stored for future use. The retentate containing the high molecular fraction was similarly handled.

Preparation of a Low Molecular Weight Extract by Precipitation of High Molecular Weight Proteins From a Solution of Total Protein Extract Using Ethanol A total protein extract of deer velvet was prepared by gently shaking dried deer velvet powder (10 g) in deionised water (100 ml) for 3 hours at room temperature. The mixture was centrifuged at 2,100 g for 15 minutes and the supernatant was decanted into a clean centrifuge bottle. The supernatant was further centrifuged at 21,000 g for 15 minutes in order to fully clarify the total protein extract solution, which was then chilled to 4° C. Cold (4° C.) 100% ethanol (3 volumes) was gradually added with constant stirring. The cloudy mixture was centrifuged at 21,000 g for 30 minutes at 4° C. to remove the precipitated high molecular weight proteins. The supernatant was transferred to a Buchi evaporation flask and the solvent was then removed under vacuum on a Buchi rotary evaporator. The amorphous dried residue, comprising the low molecular weight velvet extract, was stored at room temperature sealed in the evaporation flask prior to use.

Preparation of a Low Molecular Weight Extract by Extraction of Deer Velvet Following Pre-treatment with Ethanol
Laboratory Scale Preparation The method of choice for making this extract is by aqueous extraction following pre-treatment of the deer velvet powder with 70% ethanol. In this case 100 g of hot dipped deer velvet powder was mixed with 600 ml of 70% ethanol (food grade). The mixture was stirred for 3 hours and filtered through a sintered glass funnel. The bulk of the remaining ethanol was removed under vacuum from the velvet residue by use of a Buchi rotary evaporator. Throughout the evaporation process gentle heat was supplied to the evaporation flask by use of a water bath at 30° C. Deionised water (2 L) was added to the dried velvet and the mixture was stirred for 12 hours. After that time the extraction mixture was progressively filtered through Whatman No 1 paper, then No 6 paper, and finally glass fibre filter paper (Whatman GF/A). The velvet residue was discarded and the filtrate was centrifuged at 11,500 rpm for 10 minutes at 20° C. The supernatant was shell frozen and freeze-dried at 15° C. A total yield of 4.10 g (4.1% yield) was obtained, and was utilised for the in vitro bioassay experiments detailed below.

Pilot Scale Preparation

Powder from hot dipped deer velvet antlers, prepared as described above, was pre-treated with 70% ethanol in 34 separate batches. Each batch of between 84.0-172.6 g velvet powder was stirred for 3 hours at ambient temperature with 6 volumes (w/v) of 70% ethanol. The bulk of the solvent was removed in vacuo first by use of a rotary evaporator fitted with a 30° C. water bath (Buchi Rotavapor-R), and then with an oil pump (Edwards Speedivac ED35). The pre-treated deer velvet powder was then frozen in plastic containers before being dried on a freeze-drier (Cuddon) to remove final traces of solvent.

Potable water (86 L) was added to the combined ethanol pre-treated deer velvet powder (4.3 kg) and the mixture was stirred for 3 hours at ambient temperature. The solid residue was removed from the liquid extract by passing the mixture through a Dynocone Model 612 continuous solid bowl centrifuge (Clark Chapman, Derby UK). The velvet extract was filtered, first through a 10 μm filter bag and then a 1 μm filter bag (both GAF), before being frozen on stainless steel trays and dried in a freeze-drier (Cuddon). The freeze-dried low molecular weight velvet extract was scraped from the drier trays to provide 92 g (2.1% yield) as a light brown amorphous solid. The bulk of this material (90 g) was sterilised by γ-irradiation (Schering-Plough, Upper Hutt, NZ), during which treatment it received a minimum dose of 2.5 Mrads, and was used in the formulation and rat wound healing studies detailed below.

Gel Filtration Chromatography

Velvet extracts were analysed by Gel Filtration Chromatography on a Superose 12 HR 10/30 column (Amersham Biosciences) using 0.05 M phosphate buffer (pH 6.9) containing 0.3 M sodium chloride and 0.05% sodium azide as the elution buffer. Samples were dissolved in 0.05 M phosphate buffer (pH 6.9) at a concentration of 2-5 mg/ml and 10 μl of each solution were injected onto the column and eluted at a flow rate of 0.75 ml/min. Eluted proteins were detected by measurement of UV absorption at 280 nm.

Molecular weight calibration of the Superose 12 column was performed by separation of a standard mixture of known proteins of known molecular weights under the same conditions as used for velvet extracts. The mixture contained the following: Thyroglobulin (669 kDa); Bovine γ-Globulins (Cohn fraction 11, 160 kDa); Bovine Serum Albumin (66.7 kDa); Ovalbumin (grade V1, 46 kDa); Carbonic Anhydrase (bovine) (29 kDa); Cytochrome C (horse heart) (12.4 kDa); L-Tyrosine (181 Da). All standards were sourced from Sigma, except for L-Tyrosine which was obtained from BDH. Apparent molecular weights of eluted protein peaks were determined by interpolation using a calibration curve, which was constructed by plotting the logarithm of protein molecular weight against retention time.

SDS-PAGE Electrophoresis

A total protein extract of deer velvet and a low molecular weight velvet extract (prepared by extraction following pre-treatment with ethanol) were run on a 16.5% Tris-Tricine SDS-polyacrylamide gel (BioRad). The samples were denatured with 2-mercaptoethanol and heated to 99° C. for 4 minutes before being loaded onto the gel. 10 μl of MultiMark molecular weight marker mixture (Invitrogen), and 5, 10, 25 and 50 μg of each of the extracts were loaded onto the gel. The gels were run for 50 minutes at 190 Volts. The gels were removed and stained for 45 minutes with a 0.25% solution of Coomassie Brillant Blue G-250 (BDH), made up in equal parts of methanol and 25% trichloroacetic acid. Gels were then de-stained in a 5% trichloroacetic acid solution overnight. The gels were washed for 5 minutes in 25% methanol/1% acetic acid and then for 5 minutes in 1% methanol/0.5% acetic acid before being further fixed in a 1% glutaraldehyde solution for 5 minutes. Six washes (1.5 minutes/wash) in deionised (MilliQ) water followed.

Silver staining was conducted by adding 92.5 µl 10M sodium hydroxide to 1.44 ml 28% ammonia solution and diluting to 45 ml with MilliQ water, to produce Solution A. Solution B consisted of 0.5 g silver nitrate in 2.5 ml MilliQ water. Solutions A and B were mixed immediately prior to use, and the gel was stained in the mixture for 10 minutes. After staining the gel was washed three times in MilliQ water for a total time of ten minutes. Finally the gel was developed for approximately 1 minute in 0.005% citric acid/0.02% formaldehyde solution and the development stopped by the addition of 25% methanol/0.26% acetic acid for 2 minutes. The gels were then photographed using a Kodak DC120 digital camera for presentation.

Cell Proliferation Assay

Human umbilical vein endothelial cells were cultured in Medium 199 (GibcoBRL) supplemented with 10% fetal bovine serum (GibcoBRL), 50 U/ml penicillin, 50 µg/ml streptomycin, 2 mM L-glutamine and 1 ng/ml basic fibroblast growth factor (bFGF) in T75 tissue culture flasks (Nunclon™) in 5% $CO_2$ at 37° C. Cells were trypsinised (0.025% trypsin, 0.265 mM EDTA, GibcoBRL) and seeded in 96-well plates (Nunclon™) at a density of 3000 cells/well/200 µl and cultured for 3 days. Cells were starved in 1% serum for 24 hours and were then treated with 1% serum containing 1 ng/ml bFGF in the presence or absence of the deer velvet extracts for a further 48 hours. Two hours before the termination of incubation, 20 µl of Celltiter 96® Aqueous One Solution Reagent was added into each well. After the completion of incubation at 37° C. in a humidified, 5% $CO_2$ atmosphere, the optical densities of the wells at 490 nm ("$OD_{490}$") were recorded using a plate reader (Bio-Tek).

Migration of Bovine Aortic Endothelial Cells

Bovine aortic endothelial (BAE) cells were allowed to grow to confluence in Dulbecco's modified Eagle medium (DMEM, GibcoBRL®) containing 10% fetal bovine serum (GibcoBRL) in 12-well plates (Nunclon™). The monolayers were then 'wounded' by scraping a disposable pipette tip across the dishes. After washing with Dulbecco's PBS plus calcium (0.1 g/L) (GIBCO™, Invitrogen Corporation), the wounded monolayers were cultured for a further 48 hours in fresh 1% serum in the presence or absence of the deer velvet extracts. These were a total protein velvet extract, a low molecular weight extract made by ultrafiltration, a low molecular weight extract made by precipitation of high molecular weight proteins from a solution of a total protein extract, and a low molecular weight extract made following pre-treatment of the velvet with 70% ethanol. The latter low molecular weight extract was also tested after being boiled at 100° C. for three minutes. Some wells were included as positive controls and were instead cultured in 10% serum. The degree of movement of cells in the wounded monolayers was determined by taking photomicrographs at the time of the initial wounding and 48 hours after wounding. The photomicrographs were taken at 20× magnification on an Olympus CK2 inverted microscope and printed to a standard size of 15 cm wide by 10 cm deep. A grid with lines 1.5 cm apart and 10 cm long running parallel to a baseline was placed over the photograph. The baseline was placed on the "wounding line" above which the cells had originally been scraped off. The number of cells intercepted by each of the lines was recorded. This allowed an assessment of the number of cells that had migrated 1.5, 3.0, 4.5, 6.0, 7.5 or 9.0 cm away from the baseline on the photomicrograph.

In Situ Hybridisation

Probe Production

The in situ hybridisation protocol was based on the methods described by Clark et al. (1996). The probe, covering exons 1-4 of VEGF was cloned into the transcription vector pGEMT® Easy (Promega, Madison, Wis.). This was linearized by restriction digest with either SacII, NcoI (New England Biolabs, Beverly, Mass.), or SalI (Boehringer Mannheim, Germany) to give sense and antisense probes. Single stranded sense and antisense riboprobes were labeled by transcription with 10 µCi/µl [$^{33}$P] UTP as per manufacturers instructions (Promega, Madison, Wis.).

Section Preparation

Sections were dewaxed in xylene, then in decreasing concentrations of ethanol, then immersed in 0.2M HCl for 20 minutes (room temperature) and washed in 2×SSC (1×SSC contains 150 mM sodium chloride and 15 mM sodium chlorate, pH 7.0) for 30 minutes. Proteinase K (Sigma Chemical) digestion was undertaken at a concentration of 2 µg/ml in 200 mM Tris-HCl (pH 7.2), 50 mM EDTA (pH 8.0) at 37° C. for 15 minutes. The slides were then immersed for 2×5 minutes (room temperature) in a solution of 100 mM triethanolamine (pH 8.0), 0.25% acetic anhydride. Slides were washed in 2×SSC (room temperature) for 5 minutes, dehydrated and dried.

Hybridisation

One µl of riboprobe as labeled above under probe production (at approx 2×10$^6$ cpm/µl) was mixed with 20-60 µl hybridisation buffer. The hybridisation buffer contained: 50% (v/v) deionised formamide, 0.3 M NaCl, 10 mM Tris-HCl (pH 6.8), 10 mM sodium phosphate (pH 6.8), 5 mM EDTA (pH 8.0), 1×Denhardts solution (0.02% (w/v) each of BSA, Ficoll and polyvinyl pyrrolidone), 10% (w/v) dextran sulphate, 50 mM dithiothreitol and 1 mg/ml yeast tRNA (Life Technologies). This mixture, containing the probe, was denatured at 95° C. and applied to the pretreated and dried tissue sections which were then covered with small pieces of parafilm; no prehybridisation was undertaken. Hybridisation was performed for 18 hours at 54° C. in a sealed container humidified with 50% formamide and 0.3 M NaCl.

The slides were washed in 5×SSC at 50° C. for 15 minutes (×2) and then in 2×SSC with 50% formamide at 65° C. for 30 minutes. Four washes each of 5 minute duration, were conducted in 2×SSC at 37° C. Slides were incubated at 37° C. for 30 minutes with RNase A (Sigma Chemical) at a final concentration of 20 µg/ml in 1× wash solution (400 mM NaCl, 10 mM Tris-HCl, 5 mM EDTA, pH 7.5). The RNase A was removed by washing the slides in 2×SSC containing 50% formamide, at 65° C. for 30 minutes followed by 15 minute washes in 2×SSC and 0.2×SSC, both at 37° C. Sections were dehydrated through 30, 60, 80 and 95% ethanol containing 0.3 M ammonium acetate then two final washes in 100% ethanol alone.

Sections were air dried and coated with autoradiographic emulsion (LM-1 emulsion; Amersham International plc). The emulsion-coated slides were stored desiccated, in a light proof box at 4° C. for 3 weeks. Slides were then developed (D19 developer; Kodak, Rochester, N.Y., USA) and fixed (30% sodium thiosulphate) photographically to produce visible silver grains over the sites of hybridisation. Sections were counter stained with Gills Haemotoxylin and viewed on a Zeiss Axioplan microscope using both bright and dark field illumination.

Preparation of Formulations Containing the Low Molecular Weight Velvet Extract

Topical gel formulations of the angiogenic extract from deer velvet were prepared using three different types of polymers, namely Carbopol-934P, Pluronic F-127 and Methocel-E4M. Carbopol-934P was a gift sample from Chemcolor New Zealand Limited, Pluronic F-127 was a gift sample from BASF New Zealand Limited and Methocel-E4M FG was a gift sample from Dow Chemical Limited Australia.

Preparation of Isotonic Phosphate Buffer

Isotonic phosphate buffer (0.063M) pH 7.0 was prepared by dissolving 1.295 g of anhydrous di-sodium hydrogen orthophosphate ($Na_2HPO_4$), 0.9125 g of sodium di-hydrogen orthophosphate monohydrate ($NaH_2PO_4.H_2O$) and 1.199 g of sodium chloride in water. The volume was then made to 250 ml with water.

Formulation with Carbopol-934P

The Carbopol was prepared in isotonic mannitol solution in water.

To prepare double strength Carbopol gel, 0.5 g of Carbopol-934P was added to 50 ml of double strength isotonic mannitol solution, which was stirred using a magnetic stirrer for 30 minutes and was then kept aside to allow air bubbles to rise to the surface. The mannitol solution was made by mixing 5.07 g mannitol dissolved in water to a volume of 50 ml. The pH was adjusted to 7.0 by adding 10% (w/v) sodium hydroxide solution in water.

A double strength solution of low molecular weight velvet extract (prepared by extraction following pre-treatment with ethanol) was made by dissolving the extract at a concentration of 4 mg/ml in distilled water.

To make the control formulation, 3 g of double strength Carbopol gel was added to 3 ml of water and this was gently mixed with a spatula. It was then stored at 40° C. prior to use.

To prepare the treatment formulation, 3 g of double strength Carbopol gel were added to 3 ml of the double strength extract solution and this was gently mixed with a spatula. It was then stored at 4° C. prior to use.

Formulation with Pluronic F-127

The Pluronic F-127 formulation was prepared in isotonic phosphate buffer pH 7.0.

The double strength Pluronic gel was made by adding 20 g of Pluronic F-127 to 50 ml of cold isotonic phosphate buffer which was being gently stirred using a magnetic stirrer. Following the addition, the solution was stirred for a further 10 minutes. It was then kept at 4° C. overnight, sonicated for three hours and then stored at 4° C. overnight.

A double strength solution of low molecular weight velvet extract (prepared by extraction following pre-treatment with ethanol) was made by dissolving the extract at a concentration of 4 mg/ml in isotonic phosphate buffer.

The control formulation was made by weighing 4 g of double strength Pluronic gel and adding 4 ml of isotonic phosphate buffer to this. It was then kept in an icebox for a few minutes to convert the Pluronic gel into a solution (Pluronic in water at 4° C. is a solution and at 37° C. is a gel). It was then gently mixed with a spatula and stored at 4° C. prior to use.

To prepare the treatment formulation, 4 g of double strength Pluronic gel was taken into a vial. To this was added 4 ml of the double strength extract solution and it was then placed in icebox for a few minutes to convert the Pluronic gel into a solution. It was then gently mixed with a spatula and stored at 4° C. prior to use.

Formulation with Methocel-E4M

The Methocel-E4M formulation was prepared in isotonic phosphate buffer pH 7.0.

Double strength Methocel gel was made by slowly adding 2 g of Methocel-E4M FG to 25 ml of stirred isotonic phosphate buffer which had been heated to 80° C. An additional 25 ml of isotonic phosphate buffer, which had been cooled to 4° C., was added to the Methocel dispersion and further stirred for three minutes. The mixture was then kept at 4° C. for five hours.

A double strength solution of low molecular weight velvet extract (prepared by extraction following pre-treatment with ethanol) was made by dissolving the extract at a concentration of 4 mg/ml in isotonic phosphate buffer.

The control, of formulation alone, was made by weighing out 5 g of the double strength Methocel gel. To this was added 55 ml of the phosphate buffer and the mixture was then gently mixed with spatula. This was stored at 4° C. prior to use.

To prepare the treatment formulation, 5 g of double strength Methocel gel was taken into a vial. To this was added 55 ml of the double strength extract solution and this was gently mixed with spatula. The mixture was stored at 4° C. prior to use.

Rat Wound Healing Trials

These experiments were conducted under the conditions laid down by the Animal Ethics Committee at the Wellington School of Medicine and Health Sciences.

Male Lewis rats (aged 19-23 weeks) were acclimatised to the environment and housed individually for the duration of the experiment. The rats received normal food and water throughout the duration of the experiment supplemented with a daily oral dose of jelly (4 ml) starting on Day 0. On Day 0 animals were anaesthetised with injection (i.p.) of ketamine (100 mg/kg body weight) and xylazine (5 mg/kg body weight). Each animal had two 8 mm full skin biopsies made on the dorsal surface along the spine. The wounds were made 6 cm and 8 cm distal to the base of the skull. Care was taken to ensure each biopsy was made at right angles to the skin. The wounds were swabbed with gauze to remove excess blood and then photographed with a scale marker and identification number. The treatment and control solutions were then added to the wounds. After recovery a subcutaneous injection of Temgisic was given at 0.05 mg/kg of body weight. Reapplication of treatments and controls was at 2-3 day intervals as indicated in the figure legends (FIGS. 10-13) and during this procedure animals were lightly anaesthetized with 3.5% halothane. The wounds were photographed at the time of reapplication and then every 2-3 days until full wound closure occurred.

Dose rates and frequency of application of the low molecular weight velvet extract (prepared by extraction following pre-treatment with ethanol) were assessed in the rat wound healing model. The carrier, dosing regime, and concentration of the velvet are stated in the figure legends (FIGS. 10-13). Each animal had one wound that received 25 μl of the treatment while the other wound received 25 μl of the control substance. All experiments were performed using six animals, except for the 1 mg/ml dose (FIG. 10) which had only four animals. The photographs of each wound were taken with a Canon EOS 3000N camera (F2.8 macro lens). Prints of each exposure were recorded digitally and the area of the wound calculated from these images using NIH Image 1.63 software. The sizes of the wounds at each time point were calculated as percentages of the originals and statistical analysis was conducted by analysis of variance (ANOVA) for each time point.

Wound Histology

Wounds were made on the backs of rats as described above. A single application of PBS was made to the control wound on each rat on day 0, while the treated wound was applied on the same day with a 10 mg/ml solution of low molecular weight velvet extract (prepared by extraction following pre-treatment with ethanol) in PBS. The animals (N=6) were euthanized 4 days after wounding. The wounds were excised and for four animals the tissue was placed in 10% neutral buffered formalin for 24 hours before being transferred to 70% ethanol. Tissue from the other two animals was retained for collagen analysis. After being cut in half, the wounds were embedded in paraffin wax and the cut surfaces were sectioned. Sections were cut at 5 µm onto slides coated with APES (3-aminopropyltriethoxy-silane).

Staining of Wounds with Masson's Trichrome

Staining was undertaken as described by Bancroft and Stevens (1990). The sections were dewaxed with xylene (5 minutes×2) followed by rehydration in a series of ethanol solutions of descending concentration. The sections were then stained with Weigerts Haematoxylin for 10 minutes before being washed in running water for 10 minutes. They were placed in 0.5% Acid Fuchsin solution for 5 minutes and then rinsed in distilled water. Phosphomolybdic acid at 1% was used for 5 minutes before staining with 2% Methyl Blue for 5 minutes and washing in distilled water. Treatment with acetic acid at 1% for 2 minutes was followed by dehydration of the sections, in a series of ethanol solutions of ascending concentration, treatment with xylene and cover slipping with DePeX (BDH).

Photographs were taken on a Canon PowerShot G5 (5 mega pixel) digital camera using a Zeiss Axioplan microscope. The images were captured by remote control using the Canon Remote Control software program at a resolution of 72 pixels per inch, and were transferred into Adobe Photoshop (version 5.5) to be annotated for presentation.

Laminin Immunohistochemistry on Wounds

The sections were dewaxed with xylene (5 minutes×2) followed by rehydration in a series of ethanol solutions of descending concentration. All the reagents, antibodies and enzymes were purchased from Zymed Laboratories Inc, CA unless otherwise specified. Sections were treated with Pepsin (Cat No. 20671651) for 15 minutes at 37° C. Subsequent procedures were conducted at room temperature. After being rinsed with phosphate-buffered saline (PBS) (5 minutes×2), non-specific binding sites were blocked by treatment with 20% normal goat serum in 1% BSA/PBS for 30 minutes. The sections were then incubated for one hour with polyclonal rabbit anti-laminin antibody (1:1000 dilution) (Novus Biologicals Inc., Cat No. NB 300-144). For negative controls, the primary antibody was substituted with non-immune rabbit immunoglobulin IgG (10 µg/ml). The sections were washed in PBS (5 minutes), 0.5% non-fat milk powder/0.1% Tween-20/2×PBS (10 minutes×2) and PBS (5 minutes), followed by incubation with biotinylated secondary goat anti-rabbit antibody (5 µg/ml) for 30 minutes. The sections were washed again in PBS (5 minutes), 0.5% non-fat milk powder/0.1% Tween-20/2×PBS (10 minutes×2) and PBS (5 minutes). Zymed Peroxo-block was applied for 9 minutes to inactive endogenous peroxidases. After being washed with PBS (5 minutes×2), sections were incubated with HRP-Streptavidin Conjugate (2.5 µg/ml) for 10 minutes. The sections were washed in PBS (5 minutes×2) and developed with a 3,3'-diaminobenzidine (DAB) kit. After being rinsed in water, sections were dehydrated in a series of ethanol solutions of ascending concentration followed by treatment with xylene, and then cover-slipped using DePeX (BDH). Photographs were taken onto 400ASA Kodak black and white film using a Zeiss Axioplan microscope. The images were transferred into Adobe Photoshop (version 5.5) to be annotated for presentation.

Results

Fractionation and Gel Filtration Chromatography

Figure 2:
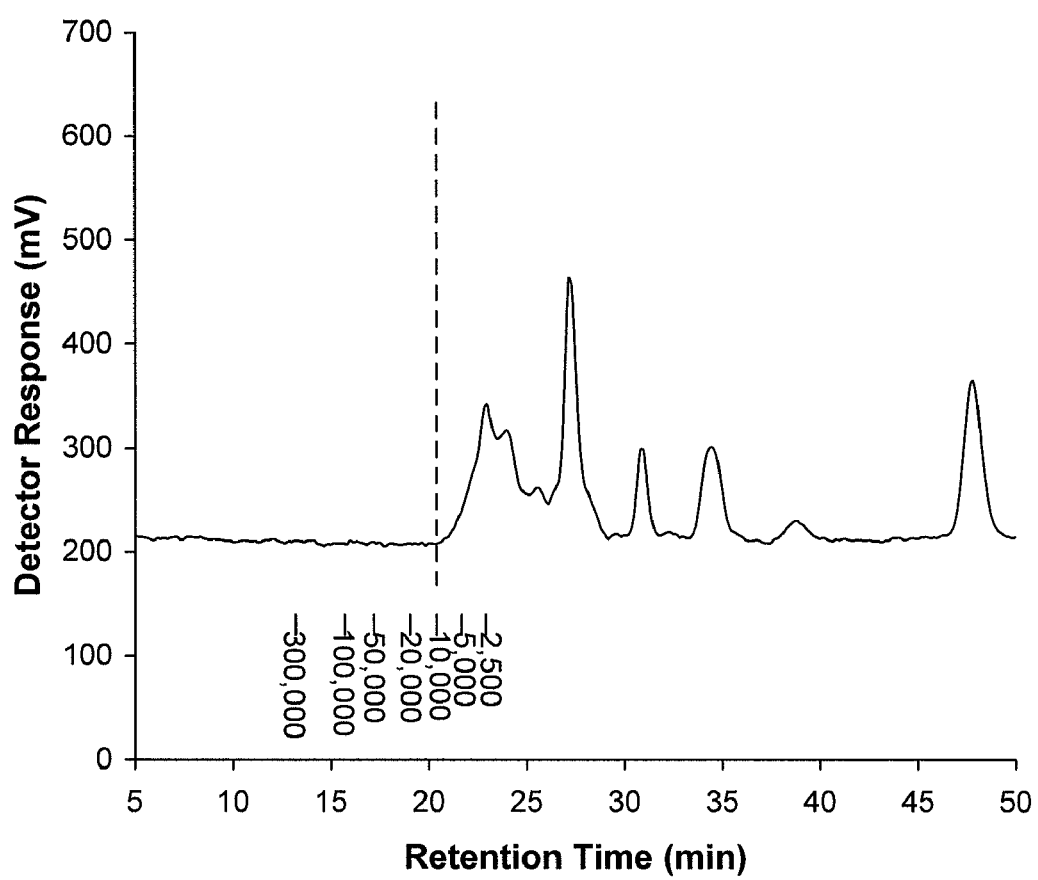
FIG. 2. Gel Filtration Chromatography Profile of low molecular weight fraction of deer velvet as derived by ultrafiltration of total protein extract. An approximate molecular weight scale is shown below the chromatogram and the Broken Line marks the expected elution position of 10 kDa proteins.

The fractionation of deer velvet by ultrafiltration through Centriprep—YM10 devices resulted in a high molecular weight fraction (FIG. 1) and a low molecular weight fraction (FIG. 2).

Figure 3:
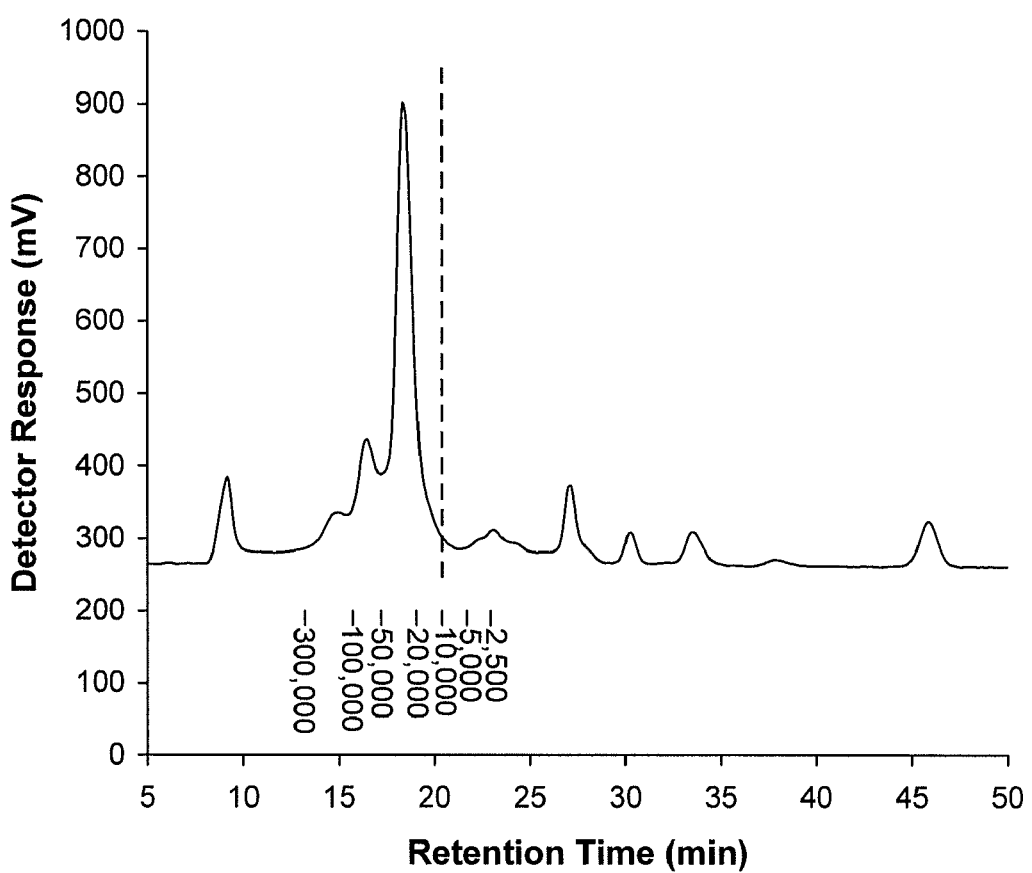
FIG. 3. Gel Filtration Chromatography Profile of total protein extract of deer velvet. An approximate molecular weight scale is shown below the chromatogram and the Broken Line marks the expected elution position of 10 kDa proteins.

A gel filtration chromatographic profile of a total protein extract is given in FIG. 3. This shows that the proteins in the total protein velvet extract had a variety of molecular weights and as expected there was a predominance of high molecular weight proteins. In comparison, an equivalent profile of the low molecular weight extract derived by pre-treatment of the velvet with 70% ethanol (FIG. 4) shows that the ethanol pre-treatment process resulted in a velvet extract containing proteins that were predominantly less that 10 kDa. Six major peaks were evident in this extract.

SDS-PAGE Electrophoresis

Figure 5:
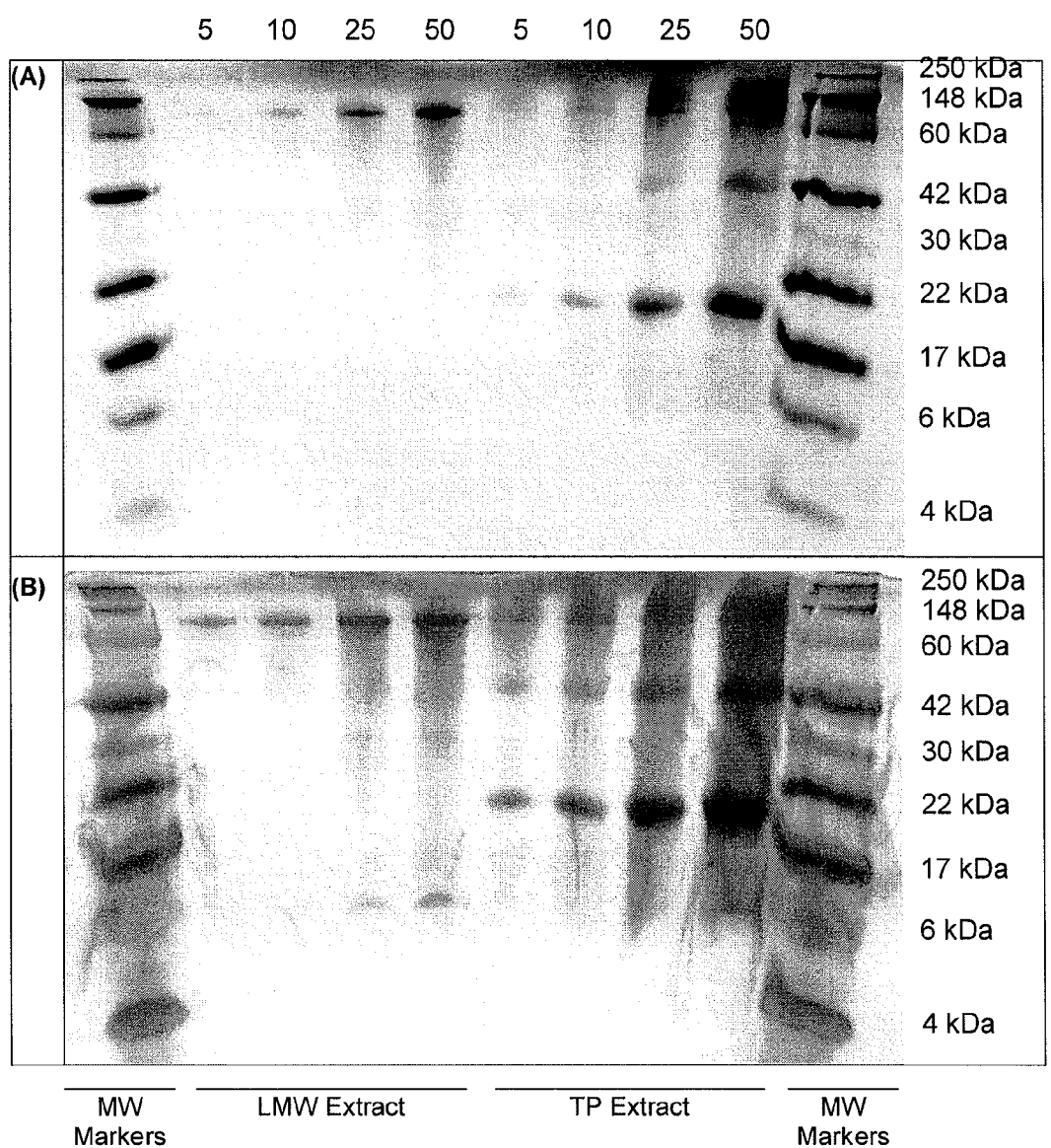
FIG. 5. SDS-polyacrylamide gel electrophoresis of Low Molecular Weight Velvet Extract as derived by extraction following pre-treatment of velvet with 70% ethanol ("LMW Extract") and of a total protein extract of deer velvet ("TP Extract"). (A) Stained with Coomassie Brilliant Blue G250. (B) Subsequently stained with silver. Lanes contained either 5, 10, 25 or 50 µg of extract. A mixture of molecular weight markers ("MW Markers") was loaded into the first and last lane of the gel, and the molecular weights of the marker proteins are indicated next to the images.

A SDS-polyacrylamide gel stained first with Coomassie (FIG. 5A) and then with silver (FIG. 5B) was used in an attempt to visualize and further characterise the proteins present within the low molecular weight velvet extract as compared to the total protein extract. The total protein extract showed a variety of proteins particularly above 60 kDa and around 20 kDa, but only two obvious bands were evident in the low molecular weight extracts lanes, either with Coomassie or silver staining. These were of around 6 kDa and over 60 kDa apparent molecular weight.

Cell Proliferation Assay

Figure 6:
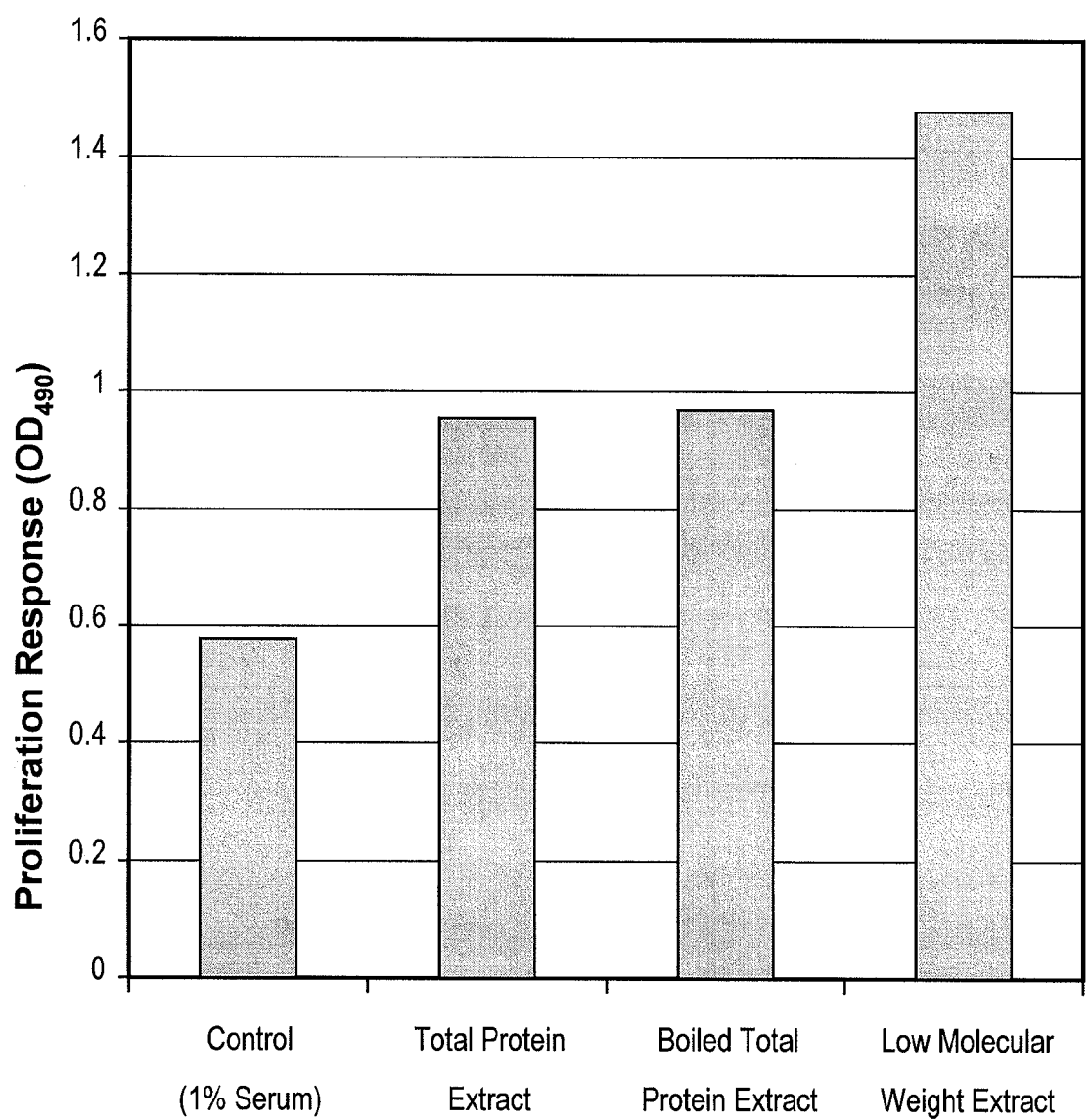
FIG. 6. A bar graph outlining the effects of different antler extracts on the proliferation of Human Umbilical Vein Endothelial Cells in response to 1% serum ("Control"), total protein velvet extract before ("Total Protein Extract") and after boiling for 3 minutes ("Boiled Total Protein Extract"), or low molecular weight extract (prepared by extraction following pre-treatment with 70% ethanol) ("Low Molecular Weight Extract"). Velvet extracts were used at a concentration of 500 µg/ml, and also contained 1% serum.

The antler extracts were able to enhance the proliferation of Human Umbilical Vein Endothelial cells in culture when compared to 1% serum (FIG. 6). This enhanced proliferation was most marked for the low molecular weight extract (made following pre-treatment of velvet with 70% ethanol). It should be noted that when the total protein velvet extract was boiled for 3 minutes it retained its proliferative activity on endothelial cells.

Migration of Bovine Aortic Endothelial Cells

Figure 7:
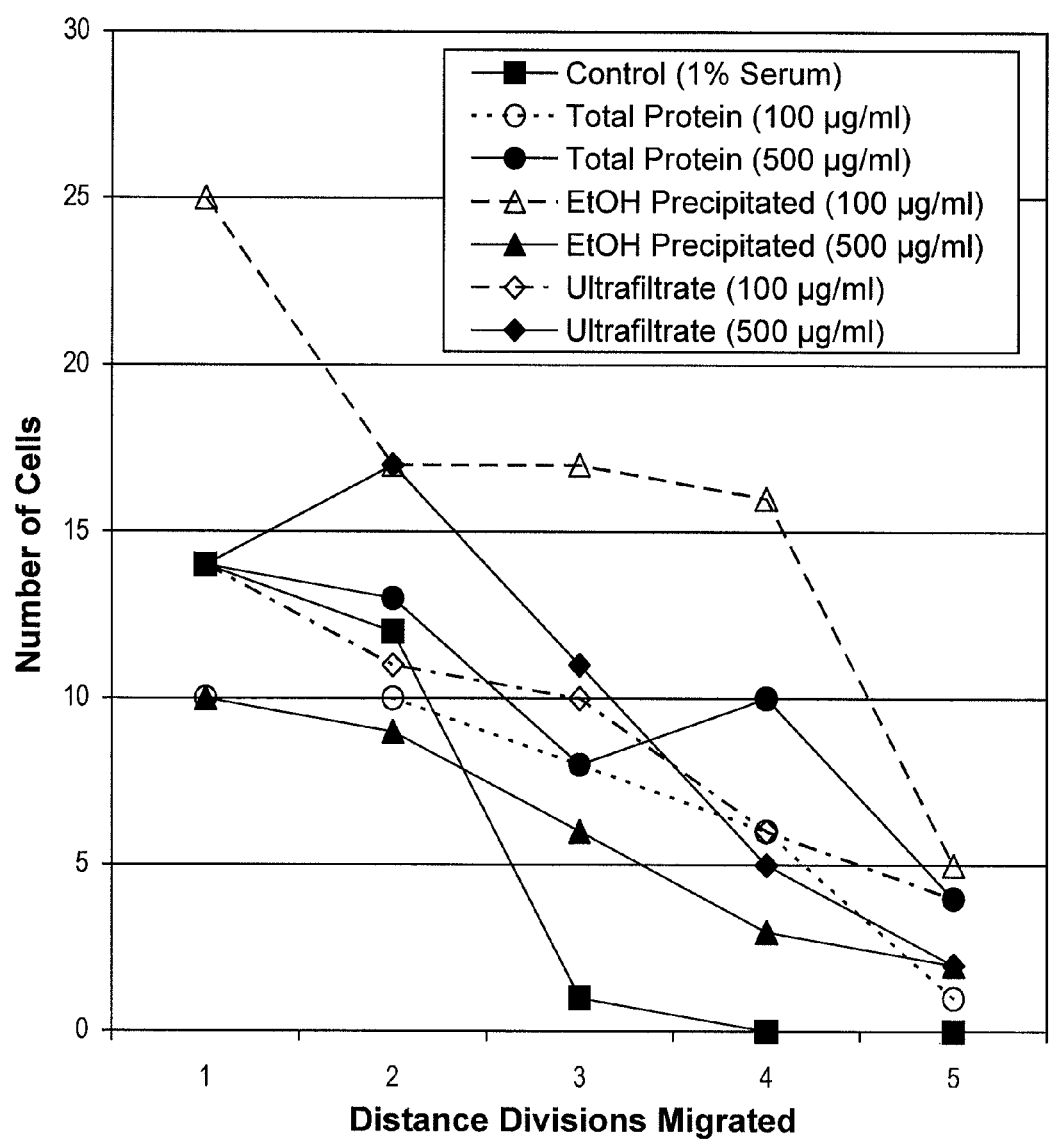
FIG. 7. A graph showing the results of a cell migration assay. The migration of BAE cells in response to 1% serum ("Control"), total protein velvet extract ("Total Protein"), low molecular weight extract made by precipitation with ethanol ("EtOH Precipitated"), or low molecular weight extract made by ultrafiltration ("Ultrafiltrate"). Velvet extracts were used at concentrations of 100 µg/ml and 500 µg/ml, and also contained 1% serum.

To further confirm the angiogenic activity of the extracts the migration of bovine aortic endothelial (BAE) cells was investigated. The low molecular weight extracts made by both the ultrafiltration and ethanol precipitation methods significantly increased the distance and number of cells migrating out from the line from which the cells were scraped away as compared to the controls (FIG. 7).

Figure 8:
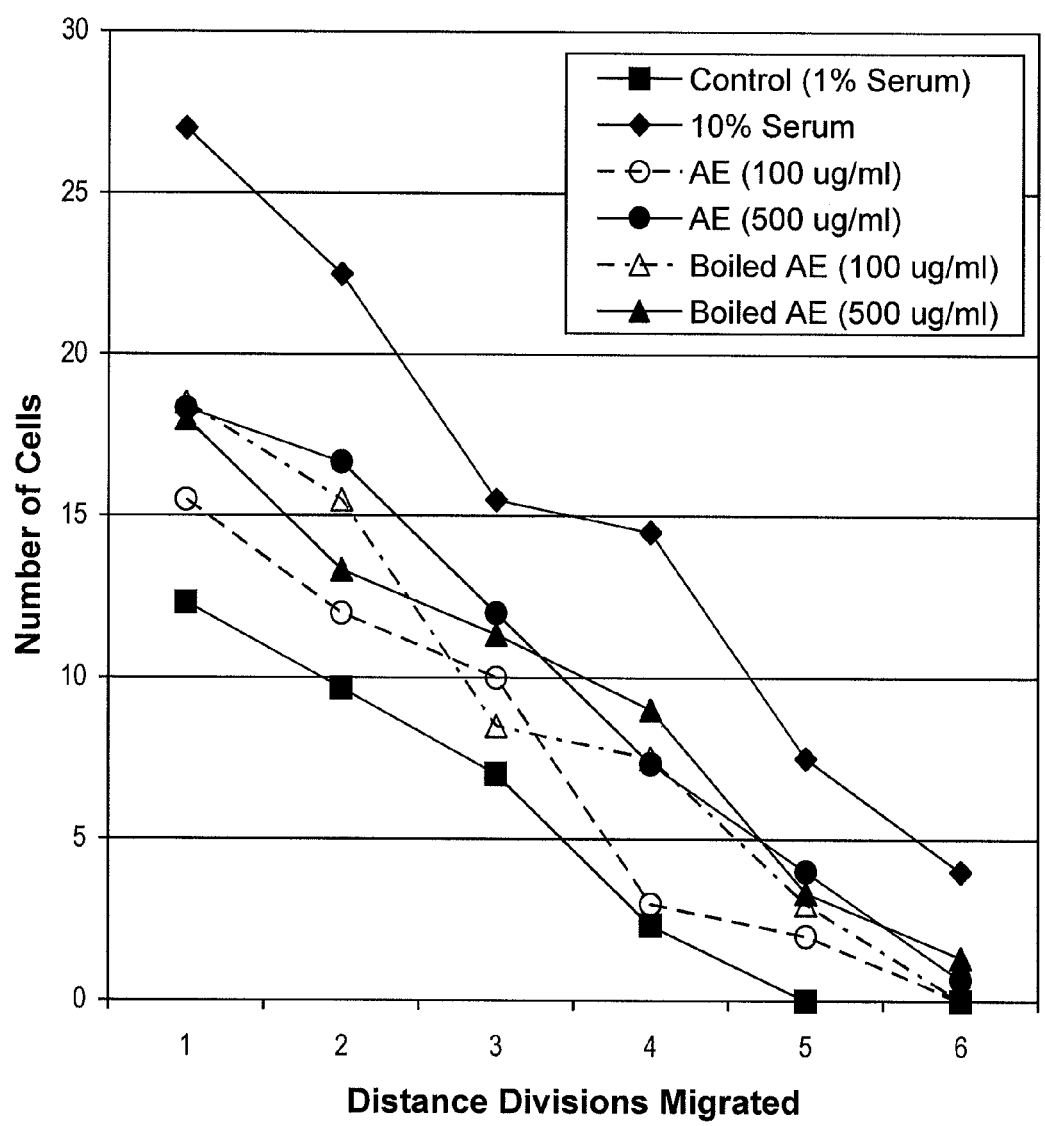
FIG. 8. Another graph showing the results of a cell migration assay. The migration of BAE cells in response to 1% serum ("Control") or the low molecular weight velvet extract (prepared by extraction of velvet following pre-treatment with 70% ethanol) before ("AE") and after boiling for 3 min ("Boiled AE"). Velvet extracts were used at concentrations of 100 µg/ml and 500 µg/ml, and also contained 1% serum.

As shown in FIG. 8, the boiling for 3 minutes of the low molecular weight extract (derived by the ethanol pre-treatment method), did not reduce the enhancing effect of the extract on the migration of the BAE cells.

In Situ Hybridisation

Figure 9:
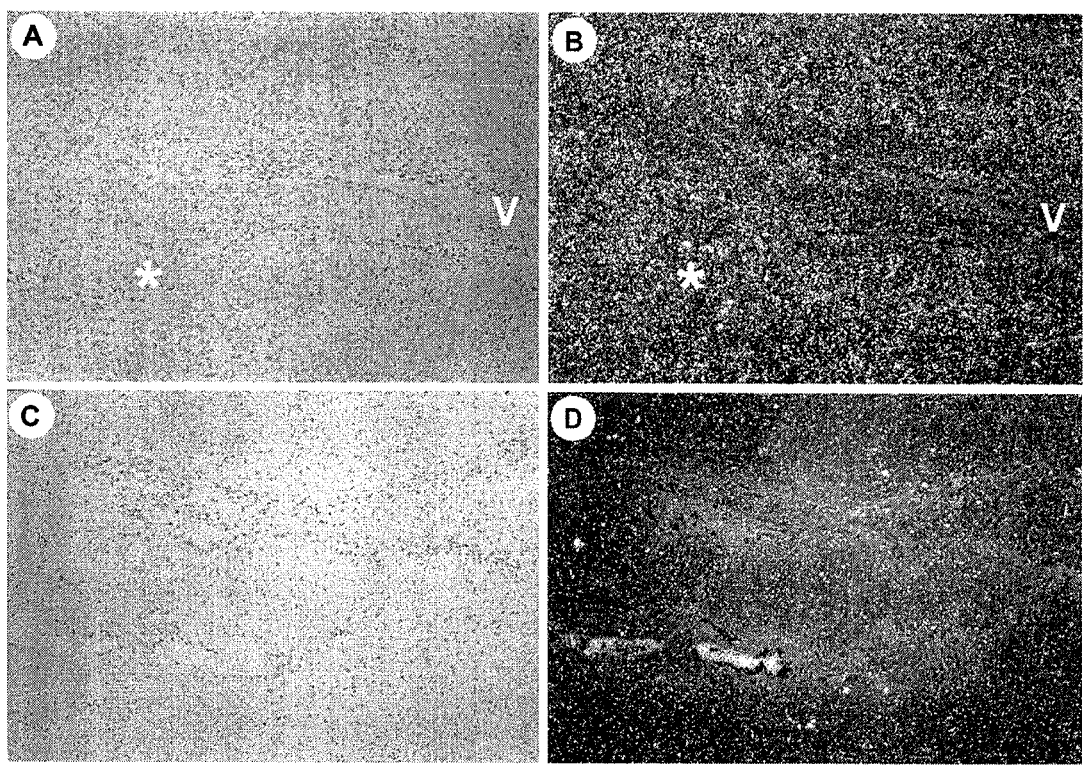
FIG. 9. Photos of in situ hybridisations using VEGF probes in the precartilage region of a velvet antler tip. A) Brightfield of antisense probe. B) Darkfield of antisense probe showing area of hybridisation. C) Brightfield of sense probe. D) Darkfield of sense probe showing only background. * Precartilage area with label. V, Blood Vessel.

In addition to this we have shown that the angiogenic activity of antler is not likely to be due to Vascular Endothelial Growth Factor (VEGF) which is the most well known of the potent angiogenic factors. In situ hybridisation was conducted using a probe covering exons 1-4 of VEGF and thus capable of detecting all the splice variants. Results in FIG. 9 reveal that VEGF mRNA was detected only in the Precartilage cells of the antler and not within the cells immediately adjacent to blood vessels. The amount of mRNA for VEGF appears to be relatively low.

We have also examined antler mRNA for some of the other classical angiogenic factors using in situ hybridization (data not shown). Surprisingly we have not been able to find significant amounts of acidic or basic Fibroblast Growth Factor mRNA suggesting that other factors must be playing an important role in driving angiogenesis within the antler.

Rat Wounding Trials

Figure 10:
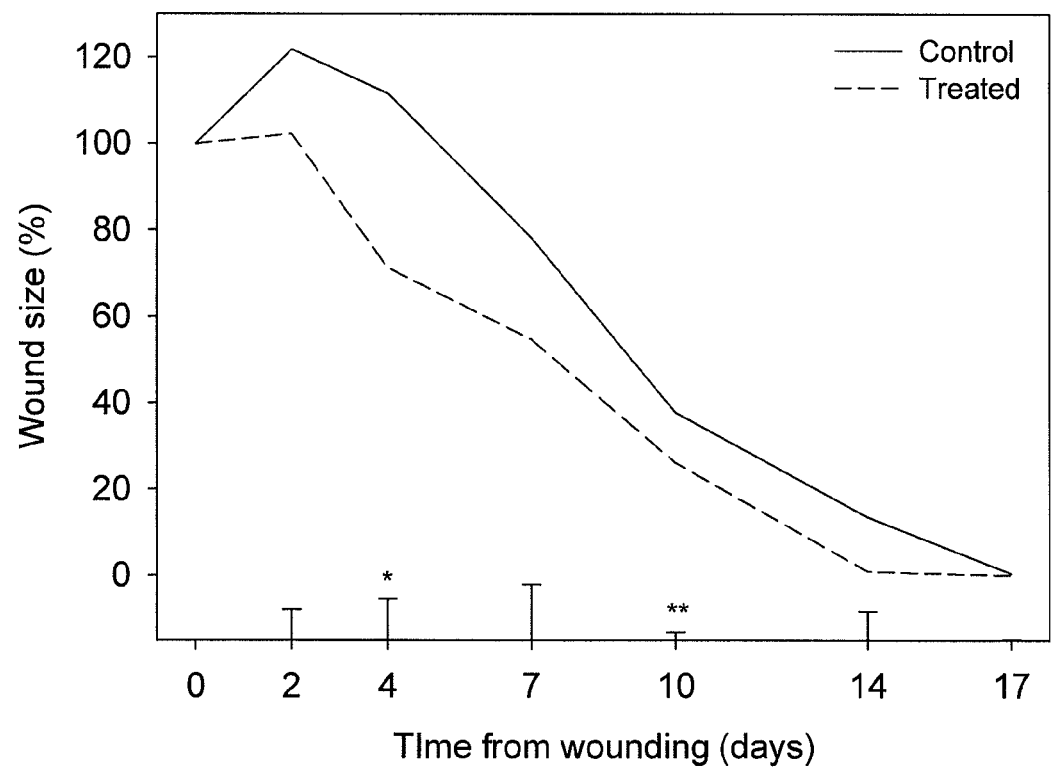
FIG. 10. A graph showing the results of a rat wound healing trial. The wounds were treated with 25 µl of saline ("Control") or with low molecular weight velvet extract (1 mg/ml in saline) ("Treated"). The low molecular weight extract was prepared by extraction following pre-treatment with ethanol. Doses were applied on days 0, 2, 4, 7 and 10. Data presented are mean wound sizes on days following wounding, as percentages of the original wound sizes. Error bars shown at days 2, 4, 7, 10, 14 and 17 are standard errors of the differences between means. The significance levels indicated with asterisks are: *P<0.05, **P<0.01.

FIG. 10 shows the percentage closure of wounds treated with saline or with a 1 mg/ml solution of low molecular weight extract made following pre-treatment of velvet with 70% ethanol. The treated wounds showed significantly faster wound healing than the control wounds treated only with saline.

The rat wounding model was used to test the dose range for treatment. The low molecular weight velvet extract (made by extraction following pre-treatment with ethanol) was compared to the carrier alone, which was PBS (control treatment). A volume of 25 μl of either solution was placed on the wounds. At a dose of 0.1 mg/ml of velvet extract there was some separation of the control and treated groups, however at no time point was the difference statistically significant (FIG. 11a). At a dose of 2 mg/ml the low molecular weight velvet extract significantly improved the rate of wound closure at days 2, 4, 6, 8, 10, and 14 (FIG. 11b). The 10 mg/ml dose of the low molecular weight velvet extract showed statistically faster wound closure on days 8 and 10 (FIG. 11c). A very high dose of the extract (100 mg/ml) similarly enhanced the rate of wound closure, with days 6, 8, 10, 12, 14 and 16 showing significant improvement (FIG. 11d).

Figure 12:
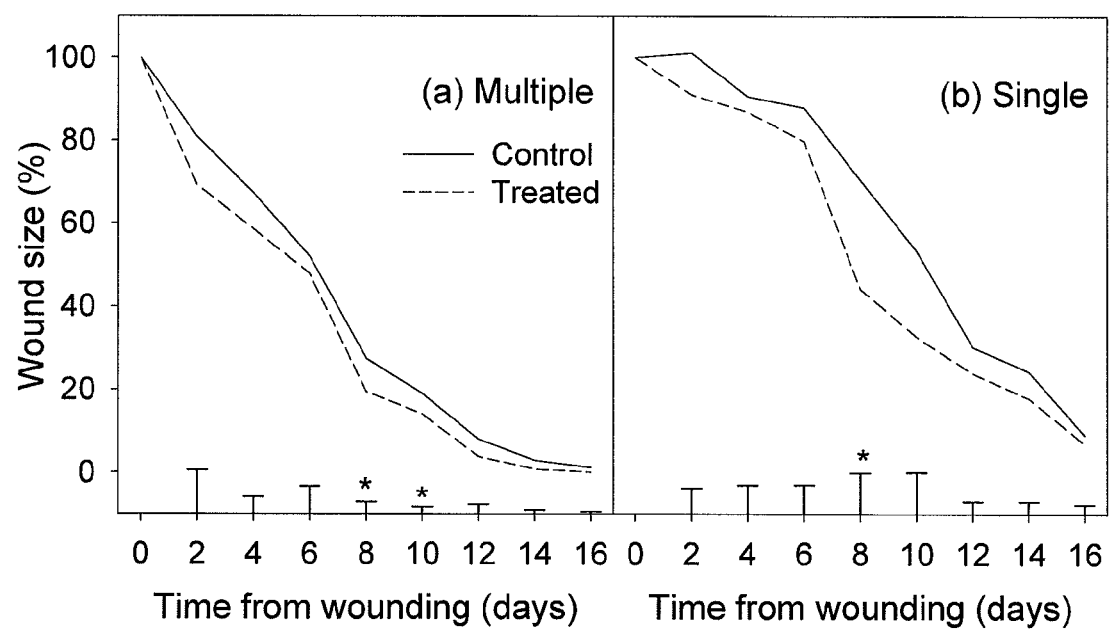
FIG. 12. Graphs showing the results of rat wound healing trials investigating the effect of frequency of application of low molecular weight extract, as derived by aqueous extraction following pre-treatment of velvet with 70% ethanol, on rate of wound closure. The wounds were treated with 25 µl of either saline ("Control") or with the low molecular weight velvet extract in saline ("Treated"). The low molecular weight extract was prepared by extraction following pre-treatment with ethanol. In (a) multiple doses were given at 10 mg/ml on days 0, 2, 4, 6, 8 and 10, while in (b) a single application was given at 10 mg/ml on day 0. Data presented are mean wound sizes on days following wounding, as percentages of the original wound sizes. Error bars are shown at days 2, 4, 6, 8, 10, 12, 14 and 16 are the standard errors of the differences between means. The significance levels indicated with asterisks are: *P<0.05, P<0.01, *P<0.001.

The effect of a single dose of the low molecular weight velvet extract (made by extraction following pre-treatment with ethanol), given at 10 mg/ml on the day of wounding, was compared with carrier alone (control) (FIG. 12). The single dose of the extract improved the rate of wound closure, with the difference between treated wounds and control wounds being statistically significant on day 8.

Figure 13:
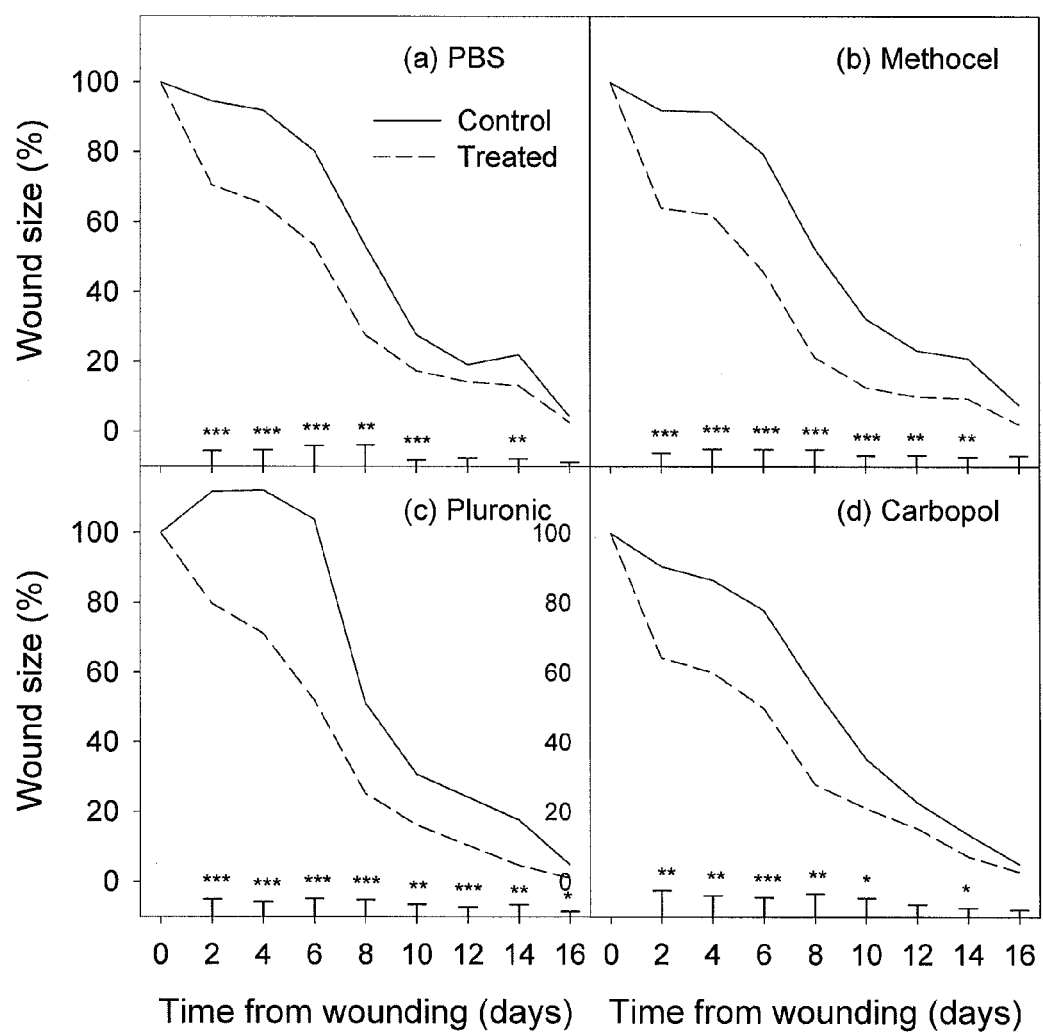
FIG. 13. Graphs showing the results of rat wound healing trials investigating the effect of different formulations of low molecular weight extract, as derived by aqueous extraction following pre-treatment of velvet with 70% ethanol, on rate of wound closure. The wounds were treated with 25 µl of various formulations either containing ("Treated") or not containing ("Control") the low molecular weight velvet extract. The low molecular weight extract was prepared by extraction following pre-treatment with ethanol. Treated wounds received the extract on days 0, 2, 4, 6 and 8 formulated at 2 mg/ml in (a) Phosphate Buffered Saline (PBS), (b) Methocel E-4M gel, (c) Pluronic F-127 gel or (d) Carbopol-934P gel. Data presented are mean wound sizes on days following wounding, as percentages of the original wound sizes. Error bars shown at days 2, 4, 6, 8, 10, 12, 14 and 16 are the standard errors of the differences between means. The significance levels indicated with asterisks are: *P<0.05, P<0.01,*P<0.001.

Various formulations of the low molecular weight velvet extract (made by extraction following pre-treatment with ethanol) were investigated at a dose of 2 mg/ml (FIG. 13). The controls in each case were the carriers alone without the extract. Formulation of the extract with Methocel significantly improved the rate of wound closure on days 2-14 as compared to the carrier alone (FIG. 13b). The extract formulated with Pluronic significantly improved the rate of wound closure on all days measured, however the carrier alone (control) had a negative impact on the initial stage of healing (FIG. 13c). When the extract was formulated with Carbopol the rate of wound closure was significantly improved on days 2, 4, 6, 8, 10 and 14 (FIG. 13d).

Wound Histology

Figure 14:
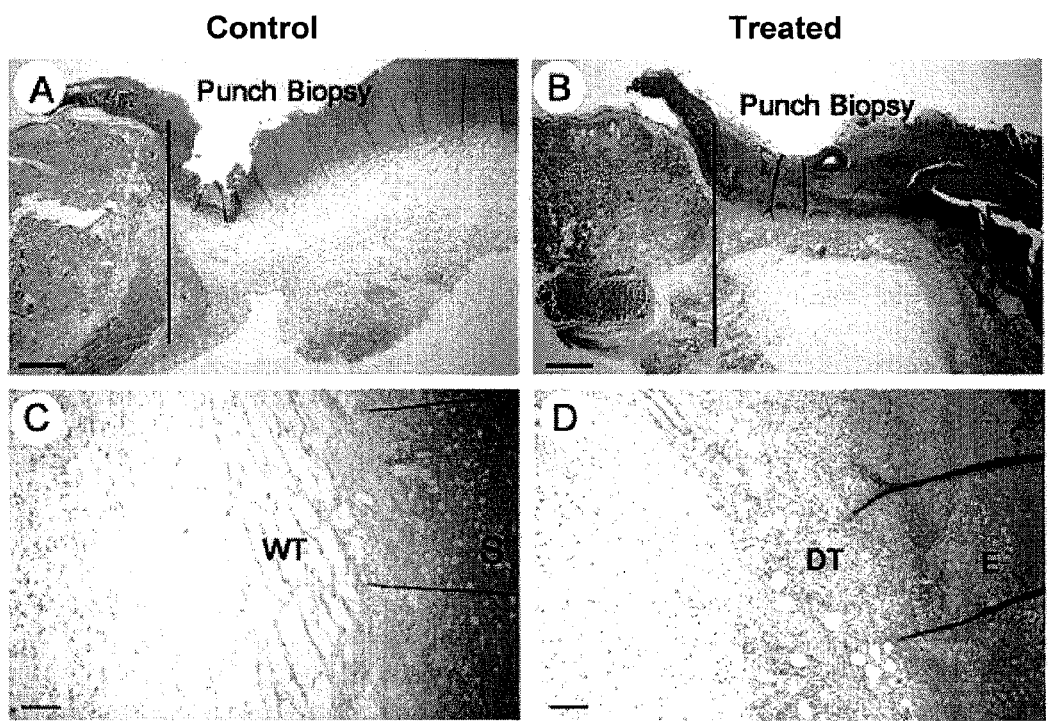
FIG. 14. Images showing wound histology as revealed by Masson's Trichrome staining of wound tissue 4 days after a single application of the low molecular weight velvet extract ("Treated") or of PBS ("Control"). The low molecular weight extract was prepared by extraction following pre-treatment with ethanol. (A) is a low magnification image of a control wound in which the Punch Biopsy (wound) is evident to the right of the horizontal line. The higher magnification image (C) of the control wounded reveals the scab (S) on the surface of the wound, and the wound tissue below (WT). A Punch Biopsy (wound) after treatment with the low molecular weight extract is evident in (B). A higher magnification (D) of the treated wound reveals dermal tissue (DT) with what appears to be vascular spaces and a forming epidermis (E). Scale bars on (A) and (B)=200 µm, and on (C) and (D)=100 µm.

Wound histology was investigated on day 4 of healing after a single application at 10 mg/ml of the low molecular weight velvet extract (made by extraction following pre-treatment with ethanol), as compared to a single dose of PBS. Six animals were used in this trial, however only four were used for histology. The healing punch biopsy site was evident with the unwounded tissue located to the left of the biopsy (FIGS. 14A, B). In the control wound the area of the punch biopsy was distinguished by the scab on the surface and wound tissue below. This wound tissue was disrupted and made up of extra cellular matrix with an interspersed cellular component (FIGS. 14A, C). The treated wound showed markedly different histology (FIGS. 14B, D). The scab (FIG. 14B) appeared in places to be taking on the resemblance of an epithelium. Underlying the surface was a layer of organized tissue we have called dermal tissue (FIG. 14D). This did not appear to be particularly rich in collagen so as to result in a scar. It appeared to have good cellular organization and have a rich network of blood vessels that would mediate a natural wound healing process. The treated wounds from 3 out of 4 of the animals were very similar to the one shown with the fourth showing less difference between treated and control wound than presented in FIG. 14.

Figure 15:
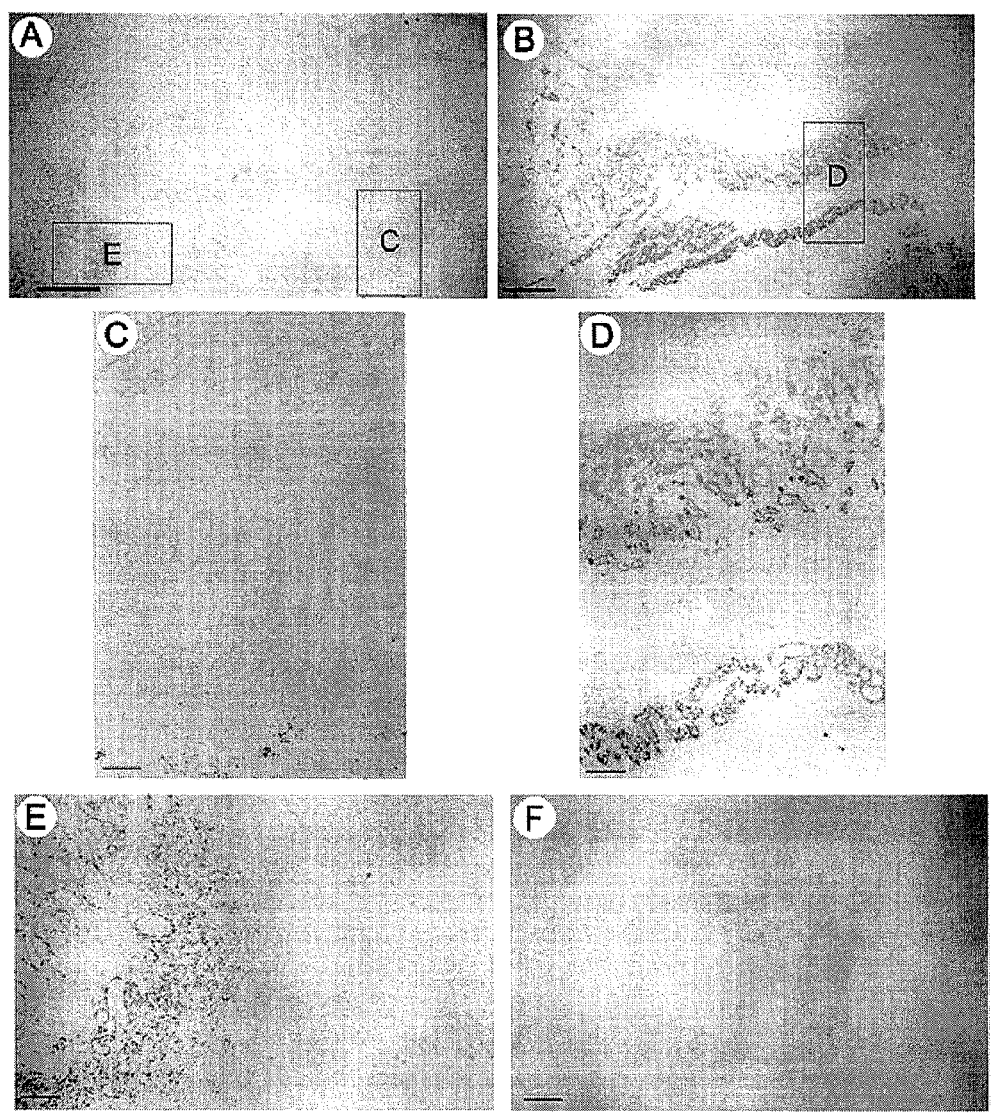
FIG. 15. Laminin immunohistochemistry of wound tissue 4 days after a single application of the low molecular weight velvet extract ("Treated") or PBS ("Control"). The low molecular weight extract was prepared by extraction following pre-treatment with ethanol. (A) In the control wound laminin was only detected within the tissue at the wound edge and not within the punch biopsy. (B) In the treated wound laminin was detected in both the wound edge and within the wound. (C) Higher magnification of the control wound in (A) with few vessels visible. (D) Higher magnification of the treated wound in (B) with basal vessels and the new vessels underlying the epithelium evident. (E) Higher magnification of the wound edge in (A) reveals the vessels only in the unwounded tissue. (F) Rabbit IgG control for the laminin antibody with no detection of signal. Scale bars on (A) and (B)=200 µm, and on (C) and (F)=100 µm.

The histological investigation was followed by immunohistochemistry for the basement membrane protein laminin. Laminin immunohistochemistry of the control wounds showed no vessels, or a reduced number of vessels compared to the treated wounds, particularly under the epithelial surface (FIGS. 15A, C). In the control wounds laminin was detected at the wound edge indicating that the antibody staining had worked on these sections (FIG. 15E). Within the treated wounds basal vessels as well as vessels underlying the epithelial surface were clearly evident (FIGS. 15B, D). The surface vessels had a different morphology to the basal vessels and stained more lightly towards the epithelial surface.

DISCUSSION

In this work attention has focused on the size of peptides and proteins contained in the extracts and fractions derived from deer velvet. This arose from the knowledge that the major component of dried deer velvet tissue is protein, and that classical angiogenic factors are also proteins. However, it is recognized that other non-protein components would undeniably have been contained in the velvet extracts and fractions described by the authors, and that these may have contributed to, or been responsible for, the observed activities.

The discovery of a low molecular weight fraction substantially less than or equal to 10 kDa which has angiogenic activity was surprising considering that many classical angiogenic growth factors are greater than 10 kDa in size (Table 1).

Figure 4:
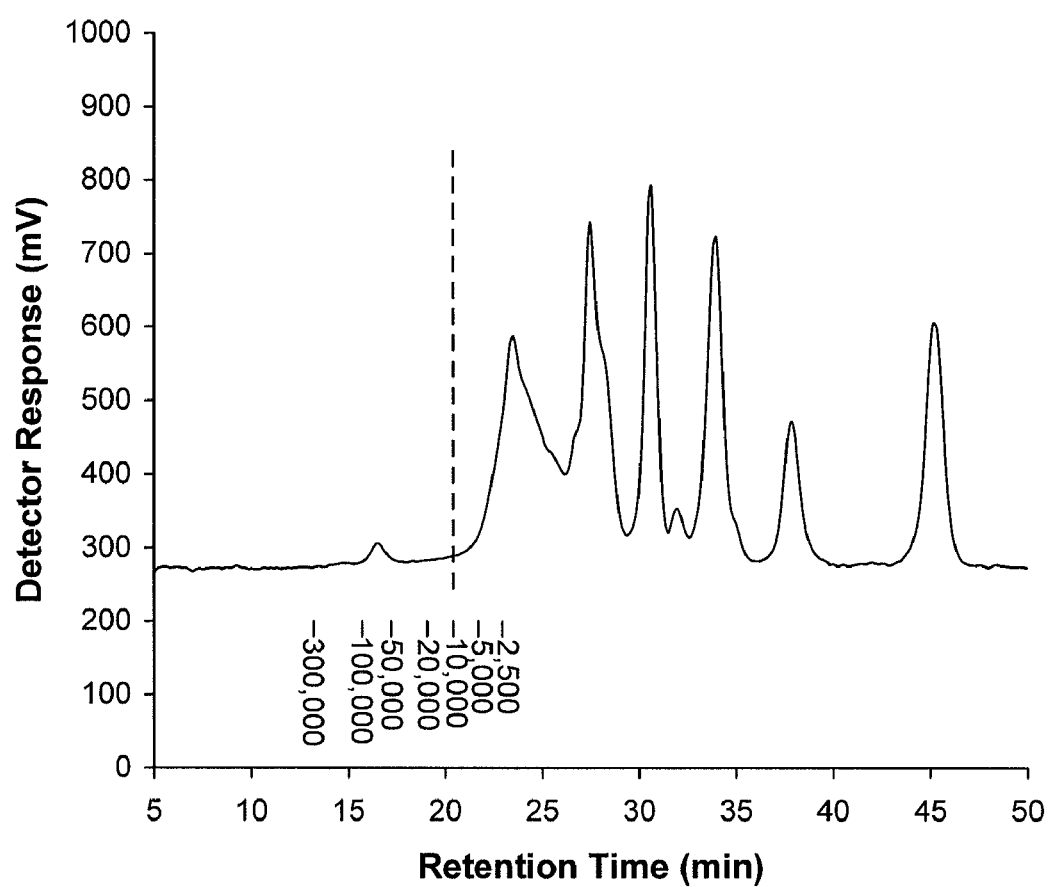
FIG. 4. Gel Filtration Chromatography Profile of low molecular weight extract as derived by aqueous extraction following pre-treatment of velvet with 70% ethanol. An approximate molecular weight scale is shown below the chromatogram and the Broken Line marks the expected position of 10 kDa proteins.

Gel filtration chromatography analysis and SDS-PAGE analysis gave apparently contrasting information on the composition of the low molecular weight velvet extract. On a SDS-PAGE gel stained with Coomassie Brilliant Blue G250 and then with silver (FIG. 5), the low molecular weight extract exhibited fewer bands than expected from the results of the gel filtration chromatography analysis (FIG. 4). In addition the proteins of molecular weights greater than 10 kDa stained relatively more intensely than was expected. However, incomplete or non-existent staining of proteins on SDS-PAGE gels is a well recognized feature of both Coomassie and silver stains (e.g. Smith, 2002; Kondratiuk et al., 1982). The lower than expected intensity of staining of the sub-10 kDa proteins in the low molecular weight extract is likely to be due to this phenomenon.

Messenger RNA for the potent angiogenic growth factor VEGF, as detected by in situ hybridization on deer antler tissue (FIG. 9), was confined to the precartilage region and was present only at low levels. In situ hybridization for aFGF or bFGF mRNA found no transcripts associated with the regions where angiogenesis occurs (data not shown). This raised the question of what factors are driving the blood vessel growth in the antler at up to 2 cm/day.

The proliferative response of Human Umbilical Vein Endothelial Cells (HUVEC) to extracts was measured. The total protein velvet extract was found to cause the proliferation of HUVEC's even after being boiled for 3 minutes (FIG. 6). The low molecular weight velvet extract (prepared by extraction following pre-treatment with 70% ethanol) caused marked proliferation of the HUVECs. When assessed in endothelial cell migration assays with Bovine Aortic Endothelial (BAE) cells the total protein velvet extract, low molecular weight extract made by precipitation with ethanol, and low molecular weight extract made by ultrafiltration, all made more cells migrate further into the scraped area (FIG. 7). The low molecular weight extract made by precipitation with ethanol showed the greatest response at 100 μg/ml, while at 500 μg/ml the response was less marked thus indicating a dose response.

The low molecular weight extract, prepared by extraction of velvet following pre-treatment with 70% ethanol, was tested for activity before and after boiling for 3 minutes (FIG. 8). The results show that the boiling had no effect on the activity at either of the doses tested. This confirmed that the molecules involved in the angiogenic activity are stable when heated for up to 3 minutes.

Figure 11:
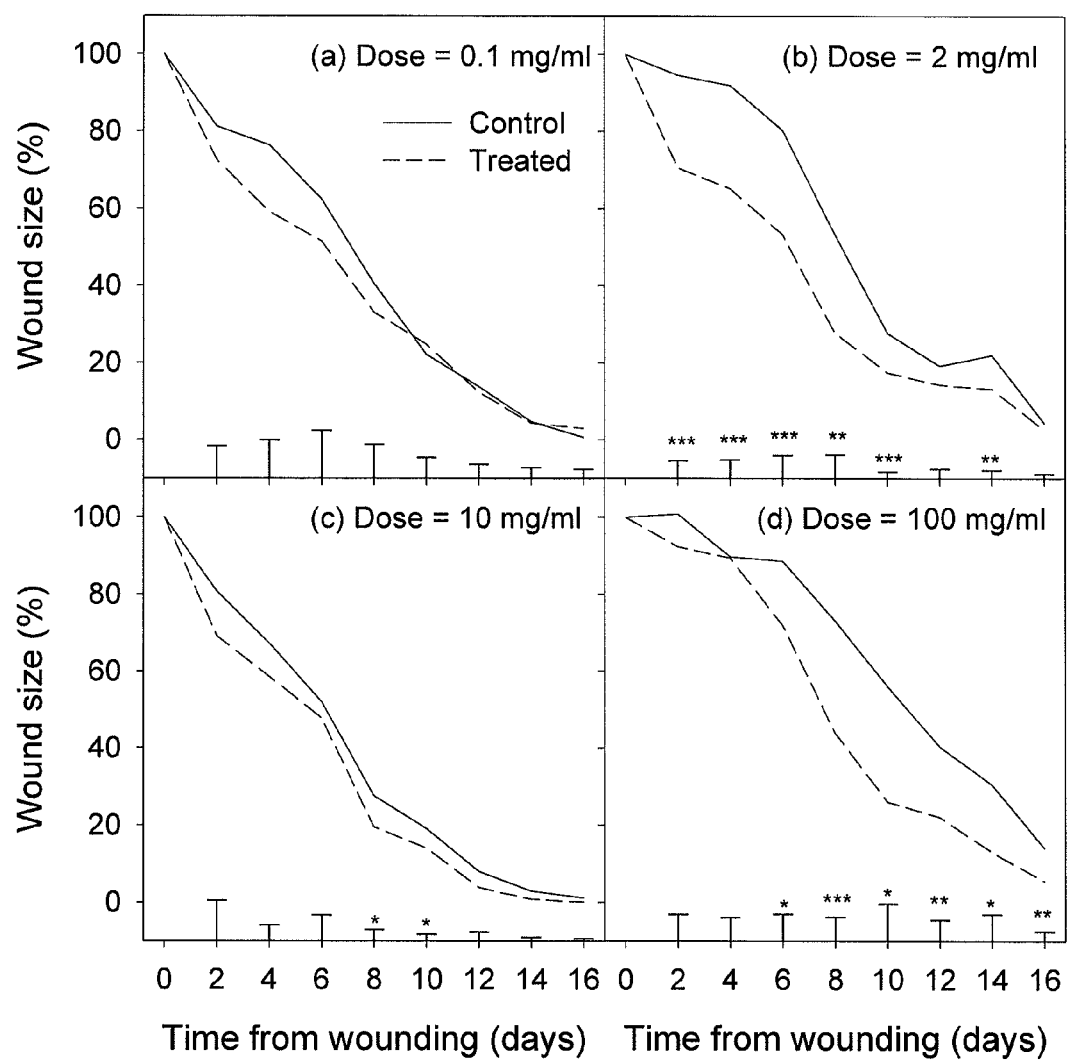
FIG. 11. Graphs showing the results of rat wound healing trials investigating the effect of dose of low molecular weight extract, as derived by aqueous extraction following pre-treatment of velvet with 70% ethanol, on rate of wound closure. The wounds were treated with 25 µl of either saline ("Control") or with the low molecular weight velvet extract in saline ("Treated"). The low molecular weight extract was prepared by extraction following pre-treatment with ethanol, and was applied at (a) 0.1 mg/ml (b) 2 mg/ml (c) 10 mg/ml (d) 100 mg/ml. Doses were give on days 0, 2, 4, 6, 8 and 10 except for 100 mg/ml which had no day 10 application. Data presented are mean wound sizes on days following wounding, as percentages of the original wound sizes. Error bars shown at days 2, 4, 6, 8, 10, 12, 14 and 16 are the standard errors of the differences between means. The significance levels indicated with asterisks are: *P<0.05, P<0.01, *P<0.001.

The low molecular weight extract, prepared by extraction of velvet following pre-treatment with 70% ethanol, has been tested in vivo on rats and found to accelerate the healing of wounds by up to three days (FIG. 10). The treated wounds were found to heal significantly faster at both the start and end of the healing process suggesting that the extract has an effect over the whole duration of healing. This deduction was confirmed by further in vivo experiments (FIGS. 11 and 13)

The results of animal wounding trials indicate a number of positive attributes for the low molecular weight velvet extract (made by extraction following pre-treatment with ethanol). For example, it retained its potent activity after exposure to a sterilising dose (2.5 Mrads) of γ-irradiation. The extract appears to have an effective dose rate for improved wound closure of between 1 mg/ml and 100 mg/ml (FIGS. 10 and 11). At no dose rate was a negative impact observed. The number of applications required to produce a response was investigated by giving a single treatment with the low molecular weight velvet extract on the day of wounding (FIG. 12). An enhanced rate of wound closure was observed compared to control wounds, with the difference reaching statistical significance at one time point (day 8). This is an interesting finding and various dosing regimes will need to be tested to ascertain which gives the optimal outcome.

Various formulations of the low molecular weight velvet extract (made by extraction following pre-treatment with ethanol) at a dose of 2 mg/ml were tested on the rat wound healing model (FIG. 13). The formulations made with Methocel and Carbopol were very similar to the formulation using PBS as a carrier and significantly improved the rate of wound closure at most time points. The Pluronic formulation may be contraindicated on the grounds that the carrier alone had a negative impact on the initial rate of wound closure (FIG. 13c). These results indicate that the extract can be delivered in a variety of formulations and still retain activity.

Wound histology was investigated using Masson's Tichrome, which is a general stain but which will effectively show the extracellular matrix proteins. The images in FIG. 14 reveal that 4 days following wounding, the dermal tissue within the low molecular weight treated wound has a structure much as would be expected for normal skin. There is evidence that the epidermis is beginning to reform and that dermal tissue containing blood vessels and an organized cellular component has migrated into the wound. The control wound remains in the early stages of wound repair with a scab and dermal wound tissue which is predominately collagen interspersed with a cellular component having no particular organisation. The histology thus suggests that the low molecular weight extract treated wounds are at a more advanced stage of healing. The histology also suggests that the extract mediates tissue repair that will result in normal wound closure and not just a collagenous scar.

The wounds were immunostained for the basement membrane protein, laminin. Laminin will be associated with the basement membrane on the basal surface of endothelium. Results revealed that, 4 days following wounding, there were more vessels within the wounded area of the low molecular weight velvet extract treated wounds with the than within the control (PBS treated) wounds. Most evident was the increase in the number of vessels within the apical/sub-epithelial zone of the treated wounds as compared to the control wounds. The control wounds had fewer, or no visible, blood vessels within the wounded area (FIGS. 15A, D, E). On the edge of the control wound, in the unwounded area, blood vessels were evident indicating that the immunostaining had worked successfully on these sections (FIG. 15E). In the low molecular weight velvet extract treated wounds the blood vessels were evident underlying the epithelium of the wound in a manner suggested by the Masson's Trichrome staining, although the immunostaining for laminin was from a different animal to that shown in FIG. 14. The blood vessels on the surface of the treated wound stained more lightly at the epithelial surface (FIG. 15D). The vessels also aligned towards the surface and this may suggest that they were developing towards the apical surface and that the basement membrane around these blood vessels was in the process of being laid down. The laminin immunohistochemistry suggests that increased angiogenesis may have resulted from application of the low molecular weight velvet extract onto the wounds.

In conclusion, the results show that compositions derived from deer velvet have angiogenic activity. In particular, the low molecular weight velvet extract, which was prepared by extraction following pre-treatment with ethanol, has potent wound healing activity. In vitro it increased the proliferation and migration of endothelial cells. On the in vivo wound healing model the low molecular weight velvet extract increased the rate of wounds closure over a dose range of 1 mg/ml-100 mg/ml. At no stage were any negative side effects seen on the animals. The morphology of the treated wounds suggests that the extract induces a healthy wound healing response that involves angiogenesis. These results indicate that treatment of wounds with the low molecular weight velvet extract is an effective way of improving the rate of wound closure and thus aiding wound healing.

TABLE 1

Examples of the molecular weights of some known angiogenic growth factors. (The size includes any unprocessed precursor.)

| Angiogenic Growth Factor | Primary Accession Number | Molecular Weight |
| --- | --- | --- |
| Vascular Endothelial Growth Factor A | P15692 | 27 kDa |
| Fibroblast Growth Factor 1 | P05230 | 17 kDa |
| Placental Growth Factor | P49763 | 25 kDa |
| Pleiotrophin | P21247 | 19 kDa |
| Angiopoietin-1 | Q15389 | 58 kDa |
| Angiopoietin-2 | Q15123 | 57 kDa |
| CYR61 | O00622 | 42 kDa |
| Thymosin β4 | P01253 | 5 kDa |

Aspects of the present invention have been described by way of example only and it should be appreciated that modifications and additions may be made thereto without departing from the scope thereof as defined in the appended claims.

REFERENCES

Auerbach R., Kubai L., Sidky Y. 1976 Angiogenesis induction by tumors, embryonic tissues, and lymphocytes. *Cancer Research* 36:3435-3440.

Bancroft and Stevens (eds.). 1990. *Theory and practice of histological techniques*, 3$^{rd}$ Edition.

Clark D. E., Smith S. K., Sharkey A. M., Sowter H. M., Charnock-Jones D. S. 1996 Hepatocyte growth factor/scatter factor and its receptor c-met; localisation and expression in the human placenta throughout pregnancy. *Journal of Endocrinology* 151:459-467.

Deodato B., Arsic N., Zentilin L., Galeano M., Santoro D., Torre V., Altavilla D., Valdembri D., Bussolino F., Squadrito F., Giacca M. 2002 Recombinant AAV vector encoding human VEGF165 enhances wound healing. *Gene Therapy* 9:777-785.

Kondratiuk T. P., Kurskiĭ M. D., Fedorov A. N., Osipenko A. A., Meshkova L. I., Litvinenko E. A. 1982. [Characterization of endogenous phosphorylation substrates of sarcoplasmic reticulum fragments from fast skeletal muscles of the rabbit]. *Biokhimiia* 47:950-6

Li C., Clark D. E., Lord E. A., Stanton J-A. L., Suttie J. M. 2002 Sampling techniques to discriminate the different tissue layers of growing antler tips for gene discovery. *The Anatomical Record* 268:125-130.

Malinda K. M., Sidhu G. S., Banaudha K. K., Gaddipati J. P., Maheshwari R. K., Goldstein A. L., Kleinman H. K. 1998 Thymosin β1 stimulates endothelial cell migration, angiogenesis, and wound healing. *The Journal of Immunology* 160:1001-1006.

Marshall J. L., Mead P., Jones K., Kaba E., Roberts A. P. 2001 The implementation of venous leg ulcer guidelines: process analysis of the intervention used in a multi-centre, pragatic, randomized, controlled trial. *Journal of Clinical Nursing* 10:758-766.

Montesinos M. C., Desai A., Chen J. F., Yee H., Schwarzschild M. A., Fink J. S., Cronstein B. N. 2002 Adenosine promotes wound healing and mediates angiogenesis in response to tissue injury via occupancy of A(2A) receptors. *American Journal of Pathology* 160:2009-2018.

Sen C. K., Khanna S., Gordillo G., Bagchi D., Bagchi M., Roy S. 2002 Oxygen, oxidants, and antioxidants in wound healing. *Annals of the New York Academy of Sciences* 957:239-249.

Smith, B. J. 2002. Quantification of proteins on polyacrylamide gels. In: Walker, J. M. (ed.). *The Protein Protocols Handbook*, $2^{nd}$ Edition. Humana Press Inc., Totowa, N.J. pp 237-242.

Sunwoo, H. H., Nakano, T., Hudson, R. J. and Sim, J. S. 1995. Chemical composition of antlers from wapiti (*Cervus elaphus*). *Journal of Agricultural and Food Chemistry* 43: 2846-2849.

What is claimed is:

1. A method of treating a persistent wound in a subject comprising the step of applying an extract of deer velvet to the persistent wound, wherein the extract of deer velvet comprises a plurality of components which have molecular weights that are substantially less than or equal to 10 kDa and which have a proliferative effect on endothelial cells and/or promote angiogenesis, said extract of deer velvet being devoid of components having a molecular weight greater than 10 kDa.

2. A method of treating a persistent wound in a subject comprising the step of applying a composition comprising a therapeutically effective amount of an isolated extract of deer velvet to the persistent wound, wherein the extract of deer velvet comprises at least one peptide having a molecular weight less than or equal to 10 kDa, which has a proliferative effect on endothelial cells and/or promotes angiogenesis, said extract of deer velvet being devoid of peptides having a molecular weight greater than 10 kDa.

3. A method of treating a persistent wound according to claims 1 or 2, wherein proliferation of endothelial cells that make up a blood vessel's endothelium lining is induced in the subject.

4. A method of claim 1 or 2, wherein, before said step of applying the extract of deer velvet to the persistent wound, said extract of deer velvet is subjected to a process selected from the group consisting of:
   heating to substantially 100° C. for up to substantially 3 minutes;
   sterilizing by exposure to over 2.5 Mrads of γ-irradiation; and
   subjecting to freeze thawing.

5. The method of claim 4, wherein said freeze thawing refers to subjecting the extract of deer velvet to substantially −20° C. and then rising to room temperature, wherein room temperature is substantially 18-25° C.

6. The method of claim 1 or 2, wherein said extract of deer velvet comprises a pharmaceutically or veterinarily acceptable carrier, excipient or stabilizer.

* * * * *

UNITED STATES PATENT AND TRADEMARK OFFICE
CERTIFICATE OF CORRECTION

| | | |
|---|---|---|
| PATENT NO. | : 8,067,364 B2 | Page 1 of 1 |
| APPLICATION NO. | : 12/470372 | |
| DATED | : November 29, 2011 | |
| INVENTOR(S) | : Coates et al. | |

It is certified that error appears in the above-identified patent and that said Letters Patent is hereby corrected as shown below:

Title Page (Item 57), in line 2 of the Abstract, After "substantially" delete "are".

Column 10, line 49, change "V1," to --VI,--.

Column 11, line 1, change "Brillant" to --Brilliant--.

Column 12, line 65, change "Haemotoxylin" to --Hematoxylin--.

Column 13, line 35, change "40" to --4°--.

Column 14, line 40, change "Temgisic" to --Temgesic--.

Column 16, line 41, change "Was" to --was--.

Column 19, line 15, change "13)" to --13).--.

Column 19, line 44, change "Tichrome," to --Trichrome,--.

Column 21, line 11 change "6" to --6.--.

Column 21, line 24 change "pragatic," to --pragmatic,--.

Column 22, line 21, in Claim 3, change "claims" to --claim--.

Signed and Sealed this
Seventeenth Day of July, 2012

David J. Kappos
*Director of the United States Patent and Trademark Office*